United States Patent
Weissenbach et al.

(10) Patent No.: US 8,921,096 B2
(45) Date of Patent: Dec. 30, 2014

(54) PUMP CART FOR A BIOLOGICAL LIQUID TREATMENT INSTALLATION

(75) Inventors: Jean-Louis Weissenbach, Ville (FR); Rene Reinbigler, Kirchheim (FR); Virginie Buisson, Wolfsheim (FR); Christine Abouayad El Idrissi, Eschau (FR); Sebastien Cirou, Schiltigheim (FR)

(73) Assignee: EMD Millipore Corporation, Billerica, MA (US)

(*) Notice: Subject to any disclaimer, the term of this patent is extended or adjusted under 35 U.S.C. 154(b) by 374 days.

(21) Appl. No.: 13/187,698

(22) Filed: Jul. 21, 2011

(65) Prior Publication Data

US 2012/0031510 A1 Feb. 9, 2012

(30) Foreign Application Priority Data

Aug. 3, 2010 (FR) ..................... 10 56421

(51) Int. Cl.
*B01D 15/14* (2006.01)
*B01D 65/00* (2006.01)
(Continued)

(52) U.S. Cl.
CPC . *F04B 17/06* (2013.01); *B01L 9/54* (2013.01); *C12M 1/12* (2013.01); *F04B 23/00* (2013.01);
(Continued)

(58) Field of Classification Search
CPC .... B01D 2201/26; B01D 15/14; B01D 65/00; B01D 2311/2688; B01D 2313/08; B01D 2313/243; F04B 17/06; F04B 23/04; F04B 23/40; F04B 29/00; F04B 23/00; F04B 53/22; C12M 1/12; C12M 1/34; C12M 21/00; C12M 23/00; C12M 23/02; C12M 23/40; C12M 23/44; C12M 23/46; B01L 9/54; G01G 19/02; B62B 1/00; B62B 1/26; B62B 5/00
USPC ............ 210/85, 86, 242.1, 252–262, 416.1, 210/232, 241, 198.2, 321.6; 417/231, 417/233–235, 238, 360, 361, 363, 474; 248/282.1, 283.1, 317, 343, 646, 647, 248/682, 690–692; 435/286.1, 286.2, 435/287.3, 289.1, 297.5, 303.1, 305.1, 435/307.1, 308.1; 414/222.01; 280/651–655; 422/565, 566; 177/140
See application file for complete search history.

(56) References Cited

U.S. PATENT DOCUMENTS

| 2,413,853 A | 1/1947 | Zademach et al. |
| 2,787,403 A * | 4/1957 | Carr et al. ................ 222/626 |

(Continued)

FOREIGN PATENT DOCUMENTS

| CN | 101281204 A | 10/2008 |
| DE | 10 2006 059 459 A1 | 7/2008 |

(Continued)

OTHER PUBLICATIONS

French Search Report dated May 24, 2011 in corresponding foreign patent application No. FR 1056421.

(Continued)

*Primary Examiner* — Joseph Drodge
(74) *Attorney, Agent, or Firm* — Nields, Lemack & Frame, LLC

(57) ABSTRACT

The invention concerns a pump cart for a biological liquid treatment installation, having a first lateral face (40), and a second lateral face (41) by which it is configured to be juxtaposed against a conveying network cart (1) of the installation and a front face (42) meeting the lateral faces (40, 41), and comprising at least one pump (414), a pump support (50) on which is mounted said pump (414), and a guide member for making said pump (414) movable in translation and on which said support (50) is mounted; said support (50) being movable in translation in a direction going from the first lateral face (40) towards the second lateral face (41); whereby said pump (414) is disposed at a predetermined location on said cart (2) depending on the type of treatment carried out.

21 Claims, 7 Drawing Sheets

(51) Int. Cl.
| | | |
|---|---|---|
| B62B 1/00 | (2006.01) | |
| B62B 5/00 | (2006.01) | |
| F04B 23/00 | (2006.01) | |
| F04B 53/22 | (2006.01) | |
| C12M 1/12 | (2006.01) | |
| C12M 1/34 | (2006.01) | |
| G01G 19/02 | (2006.01) | |
| F04B 17/06 | (2006.01) | |
| B01L 9/00 | (2006.01) | |

(52) U.S. Cl.
CPC .................................... F04B 53/22 (2013.01)
USPC .......... 435/287.3; 177/140; 210/86; 210/241;
210/258; 210/259; 248/647; 248/682; 280/651;
417/231; 417/360; 435/307.1; 435/308.1

(56) References Cited

U.S. PATENT DOCUMENTS

| | | | |
|---|---|---|---|
| 3,022,229 A | 2/1962 | Heden | |
| 3,179,117 A | 4/1965 | Gibson et al. | |
| 3,667,487 A | 6/1972 | Schoenbeck et al. | |
| 3,772,154 A * | 11/1973 | Isenberg et al. .................. | 435/33 |
| 3,774,762 A | 11/1973 | Lichtenstein | |
| 4,113,623 A | 9/1978 | Koether et al. | |
| 4,332,750 A | 6/1982 | Roggenburg, Jr. et al. | |
| 4,370,983 A | 2/1983 | Lichtenstein | |
| 4,784,751 A | 11/1988 | McGehee | |
| 4,790,118 A | 12/1988 | Chilcoate | |
| 4,852,851 A | 8/1989 | Webster | |
| 4,855,236 A | 8/1989 | Levin | |
| 4,915,119 A | 4/1990 | Franklin | |
| 5,019,257 A | 5/1991 | Suzuki et al. | |
| 5,141,866 A | 8/1992 | Levin | |
| 5,265,912 A | 11/1993 | Natividad | |
| 5,290,518 A | 3/1994 | Johnson | |
| 5,342,463 A | 8/1994 | Addeo et al. | |
| 5,520,885 A | 5/1996 | Coelho et al. | |
| 5,628,908 A | 5/1997 | Kamen et al. | |
| 5,645,723 A * | 7/1997 | Fujishiro et al. .......... | 210/321.75 |
| 5,678,568 A * | 10/1997 | Uchikubo et al. ............ | 128/897 |
| 5,711,916 A | 1/1998 | Riggs et al. | |
| 5,738,645 A | 4/1998 | Plotkin | |
| 5,985,653 A | 11/1999 | Armstrong et al. | |
| 6,073,942 A | 6/2000 | Heneveld, Sr. | |
| 6,129,099 A | 10/2000 | Foster et al. | |
| 6,146,124 A | 11/2000 | Coelho et al. | |
| 6,186,998 B1 | 2/2001 | Inuzuka et al. | |
| 6,213,334 B1 | 4/2001 | Coelho et al. | |
| 6,228,255 B1 | 5/2001 | Peterson et al. | |
| 6,232,115 B1 | 5/2001 | Coelho et al. | |
| 6,303,025 B1 | 10/2001 | Houchens | |
| 6,361,642 B1 | 3/2002 | Bellamy et al. | |
| 6,670,169 B1 * | 12/2003 | Schob et al. ................ | 435/286.5 |
| 6,808,675 B1 | 10/2004 | Coelho et al. | |
| 6,902,706 B1 | 6/2005 | Colin et al. | |
| 6,982,063 B2 | 1/2006 | Hamel et al. | |
| 7,153,286 B2 | 12/2006 | Busby et al. | |
| 7,326,355 B2 | 2/2008 | Graetz et al. | |
| 7,485,224 B2 | 2/2009 | Jones et al. | |
| 7,648,627 B2 | 1/2010 | Beden et al. | |
| 7,666,602 B2 | 2/2010 | Ammann et al. | |
| 7,867,189 B2 | 1/2011 | Childers et al. | |
| 7,935,074 B2 | 5/2011 | Plahey et al. | |
| 7,935,253 B2 * | 5/2011 | Beulay et al. .................. | 210/241 |
| 8,114,276 B2 | 2/2012 | Childers et al. | |
| 8,163,172 B2 * | 4/2012 | Beulay et al. .................. | 210/90 |
| 8,343,356 B2 | 1/2013 | Beulay et al. | |
| 8,383,397 B2 * | 2/2013 | Wojciechowski et al. . | 435/289.1 |
| 8,505,959 B2 * | 8/2013 | Darling, III .................. | 280/651 |
| 8,506,798 B2 | 8/2013 | Beulay et al. | |
| 8,557,113 B2 * | 10/2013 | Beulay et al. .............. | 210/257.1 |
| 2003/0040104 A1 * | 2/2003 | Barbera-Guillem ....... | 435/286.2 |
| 2004/0031507 A1 | 2/2004 | Ross et al. | |
| 2004/0104153 A1 | 6/2004 | Yang | |
| 2004/0222341 A1 * | 11/2004 | Breda et al. .................... | 248/200 |
| 2004/0259240 A1 | 12/2004 | Fadden | |
| 2005/0254879 A1 | 11/2005 | Gundersen et al. | |
| 2006/0024212 A1 | 2/2006 | Hwang | |
| 2006/0057030 A1 | 3/2006 | Lee et al. | |
| 2006/0118472 A1 | 6/2006 | Schick et al. | |
| 2006/0226333 A1 * | 10/2006 | Newkirk ....................... | 248/647 |
| 2007/0095364 A1 | 5/2007 | Watt | |
| 2007/0112297 A1 | 5/2007 | Plahey et al. | |
| 2007/0128087 A1 | 6/2007 | Cannizzaro et al. | |
| 2007/0199875 A1 | 8/2007 | Moorey et al. | |
| 2008/0023045 A1 | 1/2008 | Miller et al. | |
| 2008/0057274 A1 | 3/2008 | Hagiwara et al. | |
| 2008/0213143 A1 | 9/2008 | Gyonouchi et al. | |
| 2008/0254962 A1 | 10/2008 | Mizuo et al. | |
| 2009/0050756 A1 * | 2/2009 | Newkirk et al. ............ | 248/176.1 |
| 2009/0101219 A1 * | 4/2009 | Martini et al. ........... | 137/565.29 |
| 2009/0101552 A1 | 4/2009 | Fulkerson et al. | |
| 2009/0111179 A1 | 4/2009 | Hata et al. | |
| 2009/0180933 A1 | 7/2009 | Kauling et al. | |
| 2009/0215602 A1 | 8/2009 | Min et al. | |
| 2009/0294349 A1 | 12/2009 | Beulay et al. | |
| 2009/0314970 A1 | 12/2009 | McAvoy et al. | |
| 2010/0108920 A1 | 5/2010 | Tatarek | |
| 2010/0126927 A1 | 5/2010 | Blankenstein et al. | |
| 2010/0187167 A1 | 7/2010 | Reinbigler et al. | |
| 2010/0204765 A1 * | 8/2010 | Hall et al. ..................... | 607/105 |
| 2010/0206785 A1 | 8/2010 | Beulay et al. | |
| 2010/0234805 A1 * | 9/2010 | Kaufmann et al. .......... | 604/151 |
| 2011/0174716 A1 | 7/2011 | Beulay et al. | |
| 2011/0297866 A1 | 12/2011 | Weber | |
| 2011/0303306 A1 | 12/2011 | Weber | |
| 2012/0006736 A1 | 1/2012 | Cirou et al. | |
| 2012/0018018 A1 | 1/2012 | Cirou et al. | |
| 2012/0138173 A1 | 6/2012 | Cirou et al. | |
| 2012/0138522 A1 | 6/2012 | Cirou et al. | |
| 2012/0145616 A1 | 6/2012 | Weissenbach et al. | |
| 2012/0160342 A1 | 6/2012 | Weissenbach et al. | |
| 2012/0160356 A1 | 6/2012 | Reinbigler et al. | |
| 2012/0168390 A1 | 7/2012 | Beulay et al. | |
| 2012/0248025 A1 | 10/2012 | Reinbigler et al. | |
| 2013/0087490 A1 | 4/2013 | Beulay et al. | |
| 2013/0193073 A1 | 8/2013 | Hogard et al. | |
| 2013/0210130 A1 * | 8/2013 | Larcher et al. ............. | 435/288.7 |
| 2013/0236130 A1 | 9/2013 | Cirou et al. | |
| 2013/0240065 A1 | 9/2013 | Weissenbach et al. | |
| 2014/0069537 A1 | 3/2014 | Cirou et al. | |

FOREIGN PATENT DOCUMENTS

| | | |
|---|---|---|
| DE | 10 2008 003 823 A1 | 7/2008 |
| EP | 0479047 A2 | 4/1992 |
| EP | 0803723 A1 | 10/1997 |
| EP | 1195171 A2 | 4/2002 |
| EP | 1239277 A1 | 9/2002 |
| EP | 2044964 A2 | 4/2009 |
| EP | 2130903 A1 | 12/2009 |
| EP | 2208534 A1 | 7/2010 |
| EP | 2228635 A1 | 9/2010 |
| FR | 2241615 A1 | 3/1975 |
| FR | 2673853 A1 | 9/1992 |
| FR | 2931838 A1 | 12/2009 |
| FR | 2940145 A1 | 6/2010 |
| GB | 1434786 A | 5/1976 |
| GB | 2448858 A | 11/2008 |
| JP | 62-081543 A | 4/1987 |
| JP | 2010-502405 A | 1/2010 |
| WO | 00/48703 A1 | 8/2000 |
| WO | 2005/090403 A2 | 9/2005 |
| WO | 2006/043895 A1 | 4/2006 |
| WO | 2007/094254 A1 | 8/2007 |
| WO | 2008/033788 A2 | 3/2008 |
| WO | 2008/064242 A2 | 5/2008 |
| WO | 2008/071351 A1 | 6/2008 |
| WO | 2008/120021 A1 | 10/2008 |
| WO | 2009/017614 A1 | 2/2009 |
| WO | 2009/073567 A1 | 6/2009 |

(56) References Cited

FOREIGN PATENT DOCUMENTS

| WO | 2009/157852 A1 | 12/2009 |
|---|---|---|
| WO | 2010/084432 A1 | 7/2010 |
| WO | 2010/094249 A1 | 8/2010 |

OTHER PUBLICATIONS

French Search Report dated Feb. 9, 2009 in co-pending foeign patent application No. FR 0853629.
Office Action dated Jul. 22, 2011 in copending U.S. Appl. No. 13/079,188.
Written Opinion of the International Searching Authority mailed Jun. 8, 2011 in co-pending PCT application No. PCT/IB2011/050089.
International Preliminary Report on Patentability mailed Jul. 26, 2012 in co-pending PCT application No. PCT/IB2011/050089.
International Preliminary Report on Patentability mailed Dec. 20, 2012 in co-pending PCT application No. PCT/IB2011/052447.
Written Opinion of the International Searching Authority mailed Sep. 29, 2011 in co-pending PCT application No. PCT/IB2011/052676.
International Preliminiary Report on Patentability mailed Jan. 10, 2013, in co-pending PCT application No. PCT/IB2011/052676.
Written Opinion of the International Searching Authority mailed Aug. 29, 2011 in co-pending PCT application No. PCT/IB2011/052679.
International Preliminary Report on Patentability mailed Jan. 10, 2013 in co-pending PCT application No. PCT/IB2011/052679.
Written Opinion of the International Searching Authority mailed Aug. 2, 2011 in co-pending PCT application No. PCT/IB2011/052448.
International Preliminary Report on Patentability mailed Dec. 20, 2012 in co-pending PCT application No. PCT/IB2011/052448.
International Preliminary Report on Patentability mailed Dec. 20, 2012 in co-pending PCT application No. PCT/IB2011/052450.
International Search Report mailed Sep. 4, 2012 in co-pending PCT application No. PCT/IB2012/051424.
Office Action—Restriction—mailed Apr. 25, 2013 in co-pending U.S. Appl. No. 13/161,975.
Notice of Allowance mailed May 13, 2013 in co-pending U.S. Appl. No. 13/161,975.
Office Action mailed May 9, 2013 in co-pending U.S. Appl. No. 12/592,901.
Notice of Allowance mailed May 6, 2013 in co-pending U.S. Appl. No. 13/153,804.
French Search Report dated Oct. 16, 2009 in co-pending French Patent Application No. FR 0950435.
International Search Report/Written Opinion mailed Sep. 30, 2011 in co-pending PCT Application No. PCT/IB2011/052447.
International Search Report/Written Opinion mailed Sep. 28, 2011 in co-pending PCT Application No. PCT/IB2011/052450.
International Search Report mailed Jun. 8, 2011 in co-pending PCT Application No. PCT/IB2011/050089.
International Search Report mailed Sep. 29, 2011 in co-pending PCT Application No. PCT/IB2011/052676.
International Search Report mailed Aug. 29, 2011 in co-pending PCT Application No. PCT/IB2011/052679.
International Search Report mailed Aug. 2, 2011 in co-pending PCT Application No. PCT/IB2011/052448.
Office Action—Restriction—mailed Jan. 27, 2012 in co-pending U.S. Appl. No. 12/685,140.
Office Action mailed Jun. 28, 2012 in co-pending U.S. Appl. No. 12/685,140.
Extend European Search Report for co-pending foreign patent application No. EP 09290938.1, mailed Apr. 6, 2010, 5 pages.
Notice of Allowance mailed Jan. 6, 2012 in co-pending U.S. Appl. No. 13/079,188.
Office Action mailed Feb. 22, 2013 in co-pending U.S. Appl. No. 13/688,255.
Notice of Allowance mailed Apr. 1, 2013 in co-pending U.S. Appl. No. 13/161,983.
Office—Restriction—mailed Apr. 2, 2013 in co-pending U.S. Appl. No. 13/153,804.
Extended European Search Report and Search Opinion received for EP Patent Application No. 10290005.7, mailed on May 17, 2010, 5 pages.
International Preliminary Report on Patentability received for PCT application No. PCT/IB2010/050102, mailed on Aug. 4, 2011, 8 pages.
International Search Report and Written Opinion received for PCT application No. PCT/IB2010/050102, mailed on May 7, 2010, 10 pages.
French Search Report dated Sep. 24, 2010 in co-pending foreign patent application No. FR 1050209.
French Search Report dated Nov. 25, 2010 in co-pending foreign patent application No. FR 1054514.
French Search Report dated Nov. 12, 2010 in co-pending foreign patent application No. FR 1055025.
French Search Report dated Feb. 3, 2011 in co-pending foreign patent application No. FR 1055026.
French Search Report dated Nov. 22, 2010 in co-pending foreign patent application No. FR 1054517.
French Search Report dated Nov. 22, 2010 in co-pending foreign patent application No. FR 1054516.
French Search Report dated Nov. 17, 2011 in corresponding foreign patent application No. FR 1152556.
Office Action mailed Jun. 11, 2012 in co-pending U.S. Appl. No. 13/420,906.
Office Action mailed Jun. 5, 2012 in co-pending U.S. Appl. No. 12/592,901.
Notice of Allowance mailed Jun. 18, 2013 in U.S. Appl. No. 13/688,255, now US Patent No. 8,506,798.
Notice of Allowance mailed Oct. 17, 2012 in U.S. Appl. No. 13/420,906, now US Patent No. 8,343,356.
Chinese Communication, with English translation, dated Sep. 27, 2012 in co-pending Chinese patent application No. CN 201010004496.1.
Final Rejection mailed Jan. 24, 2013 in co-pending U.S. Appl. No. 12/685,140.
Notice of Allowance mailed Feb. 18, 2014 in co-pending U.S. Appl. No. 13/116,508.
Notice of Allowance mailed Feb. 3, 2014 in co-pending U.S. Appl. No. 13/430,734.
Office Action mailed Dec. 17, 2013 in co-pending U.S. Appl. No. 12/685,140.
Office Action mailed Jan. 16, 2014 in co-pending U.S. Appl. No. 13/004,425.
Notice of Allowance mailed Mar. 18, 2014 in co-pending U.S. Appl. No. 13/116,508.
Notice of Allowance mailed Apr. 14, 2014 in co-pending U.S. Appl. No. 13/116,508.
Notice of Allowance mailed Apr. 1, 2014 in co-pending U.S. Appl. No. 13/153,809.
Notice of Allowance mailed Apr. 14, 2014 in co-pending U.S. Appl. No. 13/153,809.
Final Rejection mailed Jun. 23, 2014 in co-pending U.S. Appl. No. 12/685,140.
Office Action—Restriction—mailed Oct. 15, 2013 in co-pending U.S. Appl. No. 13/004,425.
Office Action mailed Oct. 9, 2013 in co-pending U.S. Appl. No. 13/116,508.
Office Action mailed Oct. 18, 2013 in co-pending U.S. Appl. No. 13/116,508.
Notice of Allowance mailed Sep. 6, 2013 in co-pending U.S. Appl. No. 12/592,901, now US Patent No. 8,557,113.
Office Action mailed Oct. 23, 2013 in co-pending U.S. Appl. No. 13/153,809.
Notice of Allowance mailed Sep. 3, 2014 in co-pending U.S. Appl. No. 13/116,508.
Notice of Allowance mailed Sep. 2, 2014 in co-pending U.S. Appl. No. 13/153,809.

(56) References Cited

OTHER PUBLICATIONS

Notice of Allowance mailed Sep. 29, 2014 in co-pending U.S. Appl. No. 13/430,734.
Office Action mailed Aug. 25, 2014 in co-pending U.S. Appl. No. 13/004,425.
Office Action mailed Jul. 30, 2014 in co-pending U.S. Appl. No. 14/080,826.
Notice of Allowance mailed Aug. 11, 2014 in co-pending U.S. Appl. No. 13/116,508.
Notice of Allowance mailed Aug. 8, 2014 in co-pending U.S. Appl. No. 13/153,809.
Notice of Allowance mailed Jul. 2, 2014 in co-pending U.S. Appl. No. 13/430,734.
Notice of Allowance mailed Aug. 12, 2014 in co-pending U.S. Appl. No. 13/430,734.
Korean communication, with English translation, dated Jul. 31, 2014 in co-pending Korean patent application No. 10-2013-7000355.
Korean communication, with English translation, dated Jul. 31, 2014 in co-pending Korean patent application No. KR 10-2013-7001692.
Korean communication, with English translation, dated Jul. 31, 2014 in co-pending Korean patent application No. KR 10-2013-7000366.
Korean communication, with English translation, dated Jul. 31, 2014 in co-pending Korean patent application No. KR 10-2013-7000356.

* cited by examiner

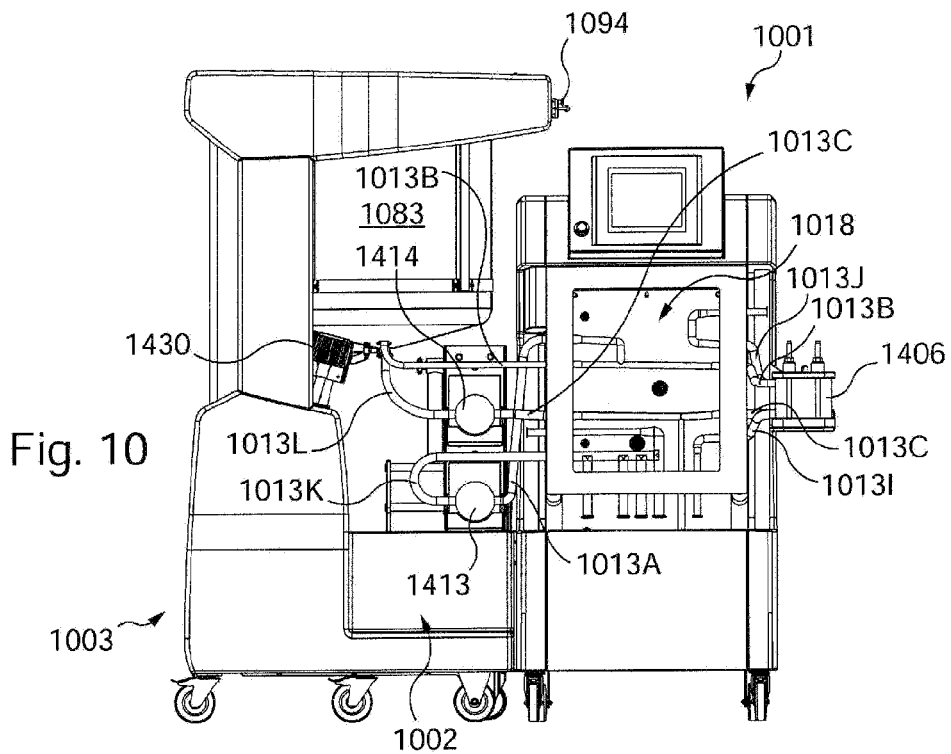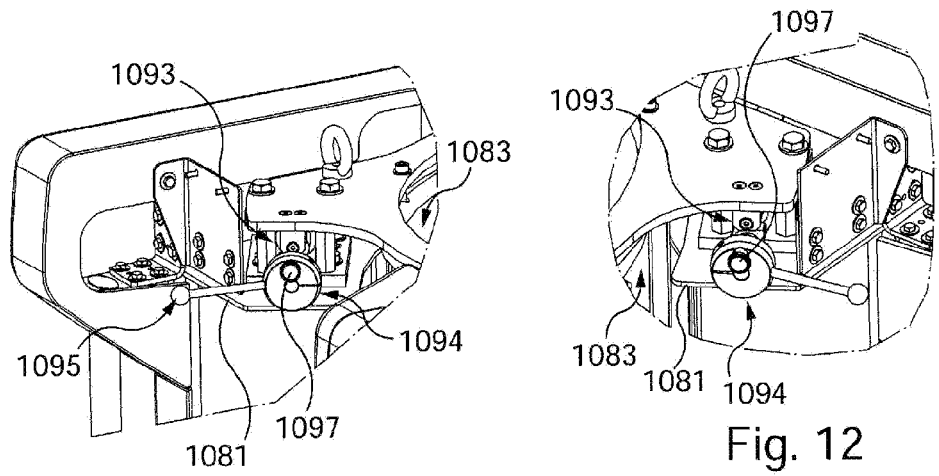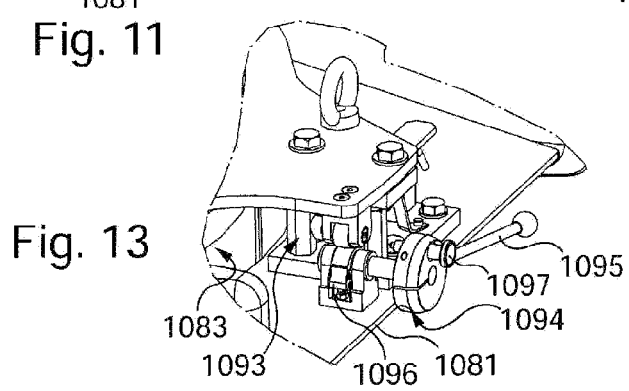

PUMP CART FOR A BIOLOGICAL LIQUID TREATMENT INSTALLATION

The invention relates to a pump cart for a biological liquid treatment installation, particularly but not exclusively for purifying a biopharmaceutical liquid in order to obtain products such as monoclonal antibodies, vaccines or recombinant proteins.

The invention also concerns a biological liquid treatment installation.

It is known that biopharmaceutical liquids are in general obtained by culture in a bioreactor and that they must then be treated to achieve the required characteristics of purity, concentration, absence of viruses, etc.

The purification is carried out by means of a succession of treatments such as clarification, to eliminate the residues from the bioreactor culture, and viral filtration sometimes followed by diafiltration and concentration by tangential flow filtration (TFF). Other operations exist concerning purification, such as chromatography (XMO).

The purification treatments are essentially carried out by filtering operations in a circuit leading to a container for collecting the treated liquid.

A number of types of container containing liquids can be connected to the inlet of the circuit, such as the source container that contains the product to be treated, but also the containers containing a cleaning liquid such as sodium hydroxide (NaOH), a rinsing liquid such as pure water for injection or a buffer liquid such as a saline solution. In addition to the container for collecting the treated liquid, various other containers for collecting cleaning, rinsing or buffer liquid, or for collecting residues, can be connected to the outlet of the circuit.

In a production context the liquid treatments can be carried out sequentially, the collecting container for the first treatment potentially becoming the source container for the next treatment, and so on until the last treatment is carried out. These treatments are conventionally carried out in dedicated installations comprising stainless steel pipes and other parts such as tanks or filter housings, which necessitate operations before and after the actual treatment, which are relatively onerous, in particular operations of cleaning after use.

Within the last few years, these treatments have alternatively been carried out in installations in which the components in contact with the liquid are single-use components.

Such single-use components have the advantage of avoiding cleaning operations, but, to provide the required degree of security, the implementation of an installation with such components necessitates operations of selection, assembly and verification which are relatively complex.

This is especially the case when the number of pipes and other circuit components (connectors, valves, etc.) is high and/or when the operating pressure is high.

According to a first aspect, the invention is directed to providing a pump cart enabling the simple, economical and convenient implementation of treatments for biological liquid.

For this, the invention concerns a pump cart for a biological liquid treatment installation, which installation further comprises a conveying network cart, said pump cart having a first lateral face, a second lateral face by which it is configured to be juxtaposed against said conveying network cart and a front face meeting the two said lateral faces;

said pump cart further comprising:
at least one pump;
a pump support on which is mounted said at least one pump; and
a guide member to render said at least one pump movable in translation and on which said pump support is mounted;

said pump support being movable in translation in a direction going from the first lateral face towards the second lateral face of said pump cart; whereby said at least one pump is disposed at a predetermined location on said pump cart depending on the type of treatment carried out.

The installation which the pump cart according to the invention makes it possible to obtain is provided to comprise disposable elements, for the most part flexible ("Flexware™"), among which are a collecting container for treated liquid, sections of circuit as well as a filtering element; and permanent or reusable elements ("hardware"), arranged in part on the pump cart according to the invention and in part on the conveying network cart juxtaposed against the second container face of the pump cart according to the invention.

The assembly of such an installation is made simply by equipping the hardware, including the pump cart according to the invention, with the disposable elements, which comprise the components adapted to cooperate with the pump. The arrangement of these permanent elements on the pump cart is also predetermined to be particularly convenient and efficient.

The position of this pump is dictated by that of the main disposable elements of the installation (such as the sections of circuit or the filtering element) with which it cooperates and which are disposed in particular on the conveying network cart (or on any other support such as a table able to be juxtaposed against the pump cart).

This arrangement ensures, firstly, fast mounting (and disassembly) of the installation by facilitating the connections of the flexible conduits and by limiting the crossing of these conduits.

Furthermore, it is convenient by virtue of the invention to position the pump in a first configuration for its connection to the elements with which it cooperates, and in a second configuration for the implementation of the treatment operations.

This arrangement also makes it possible to significantly reduce the length of the disposable conduits linking the pump to the conveying network cart.

In particular, the relative positioning between the pump and the conveying network cart is provided in order for the flexible conduit linking the pump to the pump cart to be as short and as straight as possible.

This flexible conduit may also have a minimum radius of curvature in order for avoid any risk of pinching if it is not straight.

The reduction in the length of the disposable flexible conduits enables the volume of biological liquid present in the conduits to be reduced. This makes it possible for example to achieve a smaller final volume in the case in which a treatment is carried out in which flow occurs in a loop to which belong a feed container and a filtering element from which a filtrate is evacuated (for example in a treatment by tangential filtration), since at the end of treatment the feed container is empty or nearly so and the liquid is essentially present in the conduits. This reduction in the final volume enables a higher level of concentration to be attained.

Furthermore, the fact of having a pump which is capable of being moved also makes it possible to be less strict with the tolerances associated with the lengths of the flexible conduits, for example for the connection of the pump to the conveying network cart.

Moreover, the mobility of the pump via the pump support enables the distance between the conveying network cart and that pump to be adapted when elements of the circuit (such as a bubble trap and/or a flow meter for a treatment by chromatography) have to be placed between that pump and the conveying network cart.

Thus the pump may be situated at a first predetermined location nearer to the first lateral face than to the second lateral face of the pump cart, and thus at a first specific distance relative to the conveying network cart, or at a second predetermined location nearer to the second lateral face than to the first lateral face, and thus at a second specific distance relative to the conveying network cart that is less than the first distance.

The above therefore shows that the pump cart according to the invention is very convenient in that it is adapted to equip installations carrying out variants treatments, on account of its adaptability.

According to particularly simple, convenient and economical features of the pump cart according to the invention:

said guide member comprises two arms spaced apart by slide rods which are furthermore each fastened to each of the two said arms, and the movable pump support comprises a vertical block slidingly mounted on said rods;

said vertical block comprises a system for locking said vertical block against movement in translation on said rods;

said movable pump support comprises a receptacle mounted on a face of said vertical block and configured to receive said at least one pump;

said face of said vertical block is provided with means for hooking at least one said receptacle, and said receptacle is provided with complementary hooking means for its mounting on said face of said block.

said face of said vertical block is equipped with several said hooking means provided at predetermined locations each associated with a type of treatment;

said receptacle has a cut-out on the front configured to receive a connecting head of said at least one pump.

said movable pump support and the two said arms are disposed on an upper face of said cart;

the pump cart comprises a handle which is movable between a withdrawn position and an extended position in which said movable handle enables said cart to be moved;

said movable handle is removable;

the pump cart comprises an internal space situated under said upper face and between the two said lateral faces, said space being configured to receive, at least partially, a biological liquid feed unit;

the pump cart comprises a removable panel on said lateral first face which is configured to cover said internal space; and the pump cart comprises several pumps which are mounted in superposed configuration on said movable pump support.

According to a second aspect, the invention also concerns a biological liquid treatment installation comprising:

a pump cart as described earlier;

a conveying network cart juxtaposed against said second lateral face of said pump cart, which conveying network cart comprises a portion of circuit having a plurality of connectors and a network for conveying liquid between said connectors, said conveying network being formed by a plurality of conduits, and a press comprising a first shell and a second shell mounted on said first shell, said first shell and second shell cooperating to form said conduits of said conveying network; and a biological liquid feed unit juxtaposed against said first lateral face of said pump cart or mounted on said pump cart, which feed unit is configured to feed said at least one pump with biological liquid;

said at least one pump being located facing a connector of a said conduit and being configured to make said biological liquid flow in said conduit.

The fact that the outlet point from the pump is situated facing a connector of a conduit of the circuit portion makes it possible to optimize the length of the disposable conduit linking that outlet point to that connector.

Furthermore, the conveying network cart and the feed unit enable the mounting of the installation according to the invention to be facilitated.

To be precise, it suffices for the operator to bring together the two carts and the feed unit in order for the main components of the installation (feed unit, pump, conduits of the conveying network and filtering element) to be optimally positioned relative to each other. All that remains to do is to connect those components by installing the disposable elements, and the mounting of the installation is finished.

Lastly, just as preparation of the installation is facilitated by the arrangement of its main components in the two carts and the feed unit, the operations to be carried out on the installation, after the treatment operation that it has made possible to carry out, are particularly simple to implement because it is essentially a matter of scrapping the disposable elements with which the two carts and the feed unit are equipped, the removal operations being just as simple to carry out as the mounting operations.

According to a preferred feature that is particularly convenient for use of the installation, at least one of said conveying network cart and said feed unit is configured to be nested at least partially within said pump cart.

The fact that, of the feed unit and of the two carts, at least two of them can be nested together, and are consequently separable, facilitates the mounting of the installation, which is thus modular with modules formed by the two carts and the feed unit, and in particular the mounting of certain sections of circuit.

Furthermore, this at least partial nesting enables optimization of the footprint on the ground required for the installation according to the invention.

This possibility of optimizing the footprint is particularly advantageous when, as is generally the case in the treatment operations for biopharmaceutical liquids, the installation is disposed in a controlled atmosphere area where space is at a premium.

According to a preferred feature which is particularly convenient for the transport of the installation, and in particular of its feed unit, said feed unit comprises a tank configured to receive a feed container provided to contain said biological liquid, at least one measuring cell for measuring the weight of said tank, said tank resting on said at least one measuring cell when said feed unit is in a working configuration, and at least one member for receiving weight of said tank configured for said tank to rest on said at least one measuring cell no longer when said feed unit is in a resting configuration.

Advantageously, as the measuring cell for measuring the weight of the tank is particularly useful during the treatment operations, the member for receiving weight of the tank enables that measuring cell for measuring the weight of the tank to be relieved, whether that tank is full or empty, when the treatment is not carried out, and for example when transportating the feed unit.

According to features that are preferred as being favorable to the simplicity and convenience of use of the installation of the invention:

said at least one measuring cell is interposed between two plates, one of which is fastened to said tank and the other to said feed unit, and said weight receiving member is formed by a cam interposed between the two said plates and by a crank configured to move said cam so as to move the two said plates apart; and said feed unit comprises the same number of weight receiving members as there are measuring cells.

According to still another particularly convenient preferred feature of the installation, said feed unit has a first lateral face provided with a plurality of valves and a second lateral face which is an opposite face to said first lateral face and which faces said pump cart.

Where appropriate, the feed unit does not comprise a tank provided with a feed container but has as main function to allow or prevent (by virtue of the valves) the passage to the pump of liquid coming from various containers, containing for example source liquid, in the manner of a distributor.

According to a particularly convenient preferred feature of the installation, said second conveying network cart comprises a base having a front face, a movable or removable door, said first shell being disposed on said front face of said base and said second shell being disposed in said door, said conveying network cart having a closed door position in which said conduits are formed, said second shell furthermore being of transparent material and said door being at least partly of transparent material, whereby the conveying of biological liquid in said conduits of said conveying network is visible from the exterior of the installation.

Advantageously, it is possible for the operator to monitor the conveying of biological liquid within the conduits of the conveying network of the conveying network cart, despite the door and the second shell, which must each be of sufficient thickness, and in particular the second shell, to withstand the forces of pressure exerted within the press.

The disclosure of the invention will now be continued with the description of embodiments, given below by way of illustrative and non-limiting example, with reference to the accompanying drawings, in which:

FIG. 10 is a front view of the second installation, in nested configuration, with connecting pipes in place;

FIGS. 11 to 13 are partial views in perspective of a feed unit for biological liquid of the second installation showing in detail members for receiving weight of a tank.

Figures 1, 2:
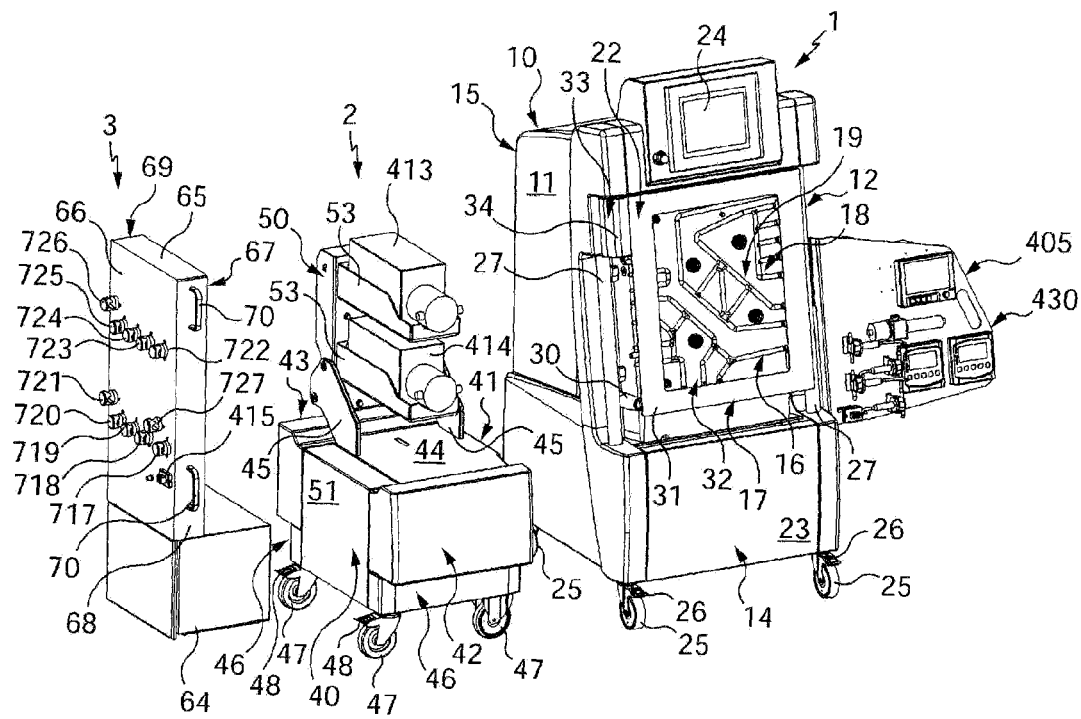
FIG. 1 is a perspective view of a first installation for treatment of liquid by chromatography, in separated configuration.
FIGS. 2 and 3 are perspective views, respectively from the front and from the back, of the first installation, in nested configuration.

Referring to FIG. 1, there can be seen a first installation for treating a biological liquid by chromatography, comprising a first cart which is conveying network cart 1, a second cart which is a pump cart 2 and a biological liquid feed unit 3, in a separated configuration, that is to say with the first cart 1 away from the second cart 2, and with the feed unit 3 away from the second cart 2, which is located between the first cart 1 and the feed unit 3.

Figure 3:
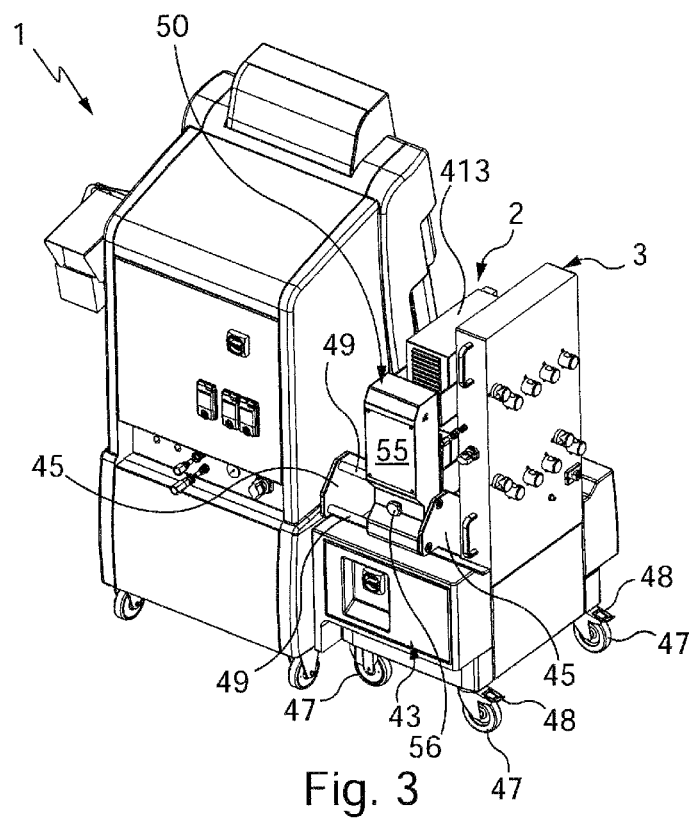
Figure 4:
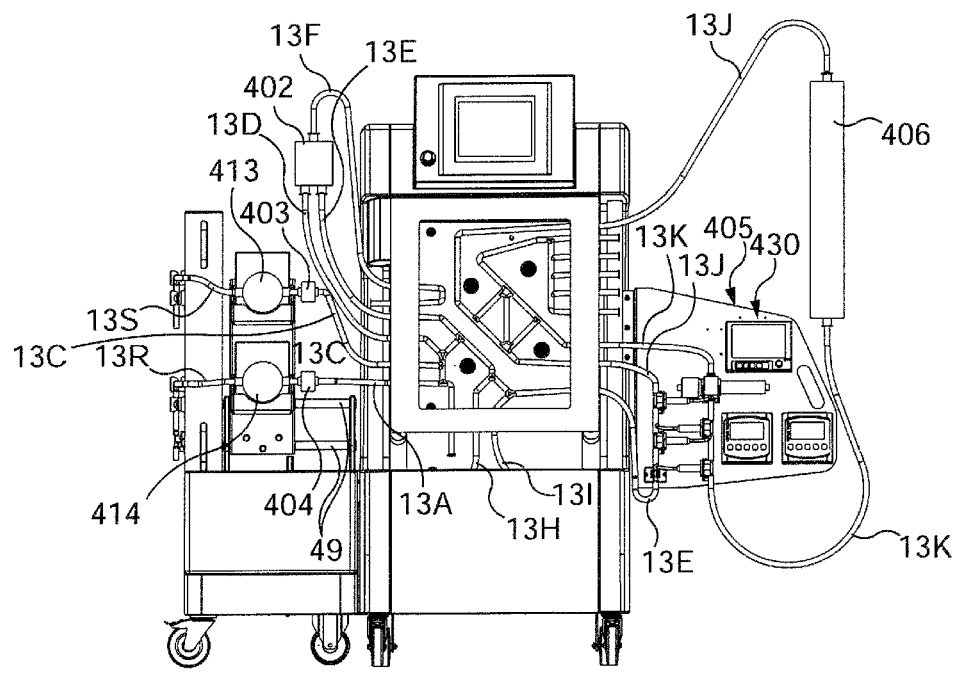
FIG. 4 is a front view of the first installation, in nested configuration, with connecting pipes in place.
Figure 5:
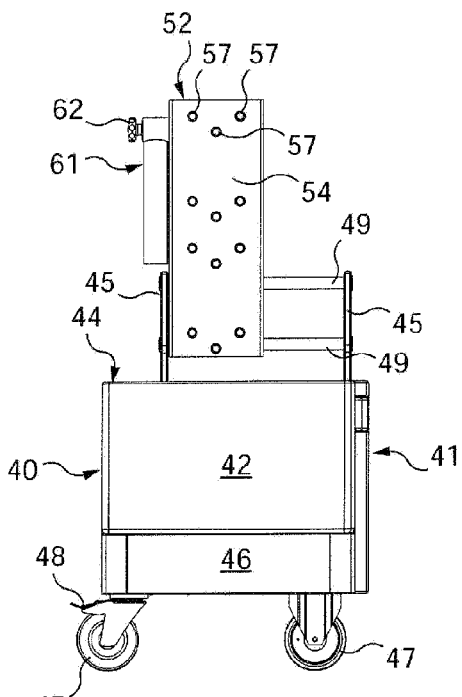
FIGS. 5 and 6 are front views of a pump cart of the first installation, respectively without and with pump support parts.
Figure 6:
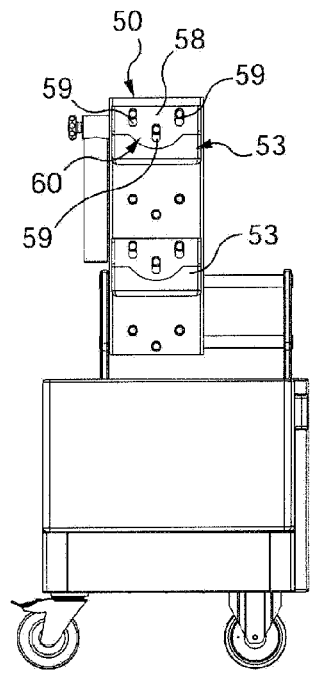

Referring to FIGS. 2 to 4, the same installation with two carts 1 and 2 and a feed unit 3 can be seen, in a nested configuration, that is to say with the second cart 2 juxtaposed by one of its lateral faces against the first cart 1, and the feed unit 3 partially nested in the second cart 2 by the other of its lateral faces.

Figure 7:
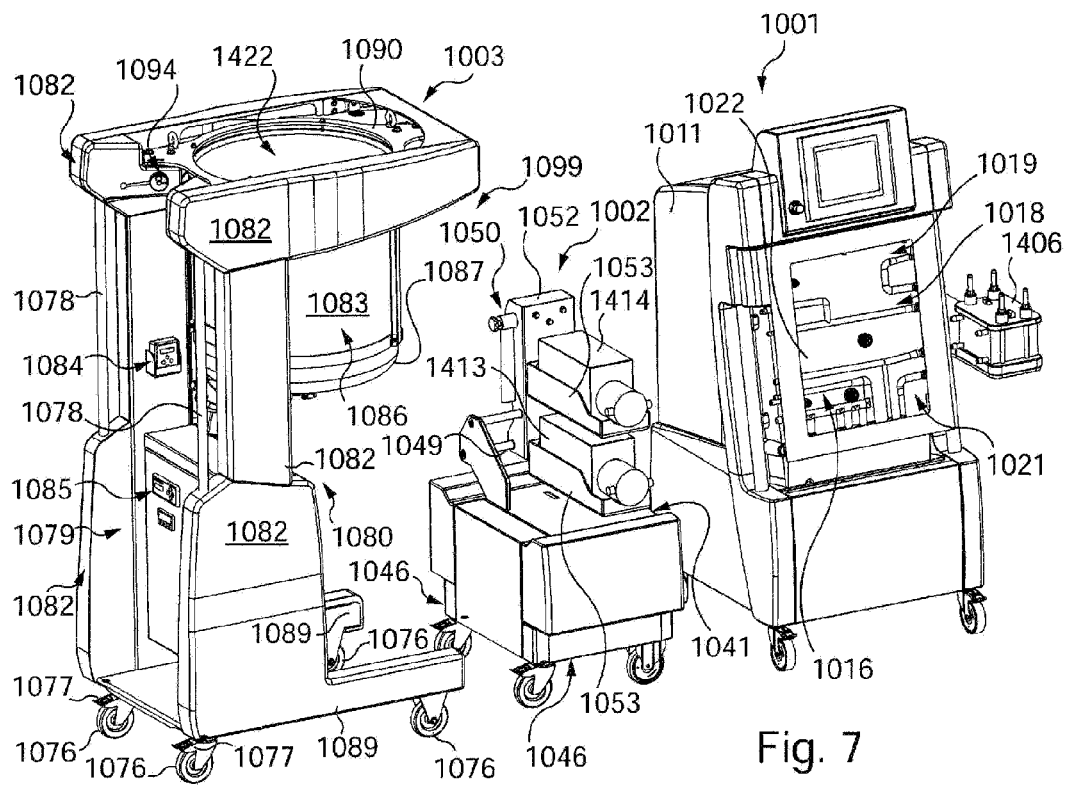
FIG. 7 is a perspective view of a second installation for treatment of liquid by tangential filtration, in separated configuration.

Referring to FIG. 7, a second installation for treating a biological liquid by tangential filtration can be seen, comprising a first cart which is a conveying network cart 1001, a second cart which is a pump cart 1002 and a third cart 1003 for biological liquid feed, in a separated configuration, that is to say with the first cart 1001 away from the second cart 1002, and with the third cart 1003 away from the second cart 1002, the latter being located between the other two carts 1001 and 1003.

Figure 8:
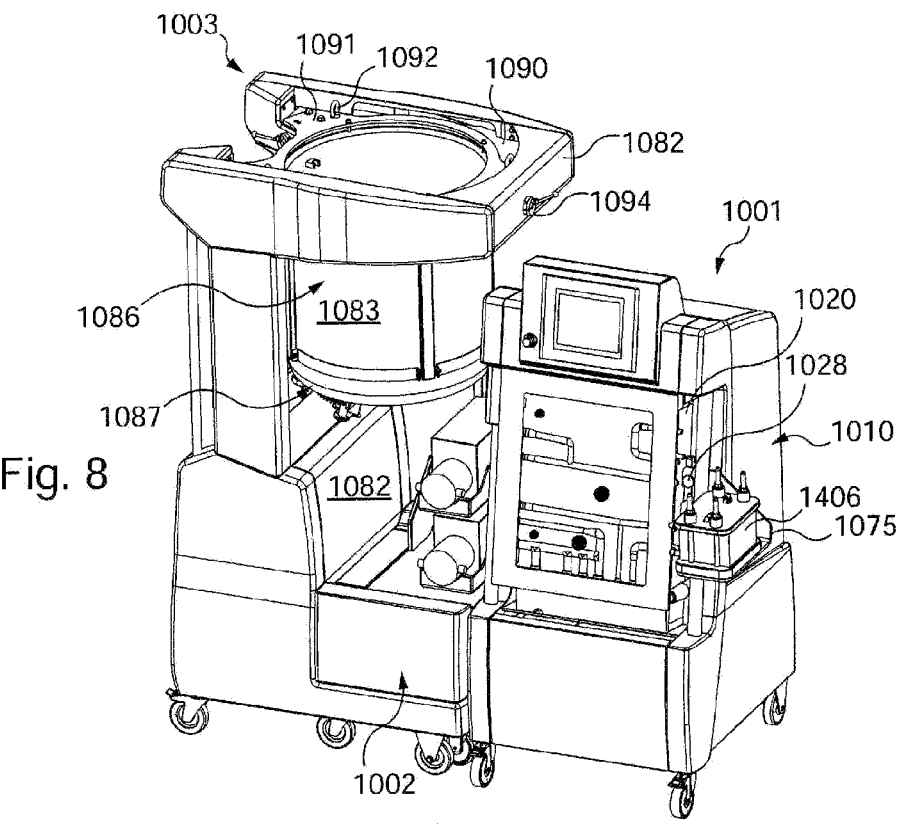
FIGS. 8 and 9 are perspective views, respectively from the front and from the back, of the second installation, in nested configuration.
Figure 9:
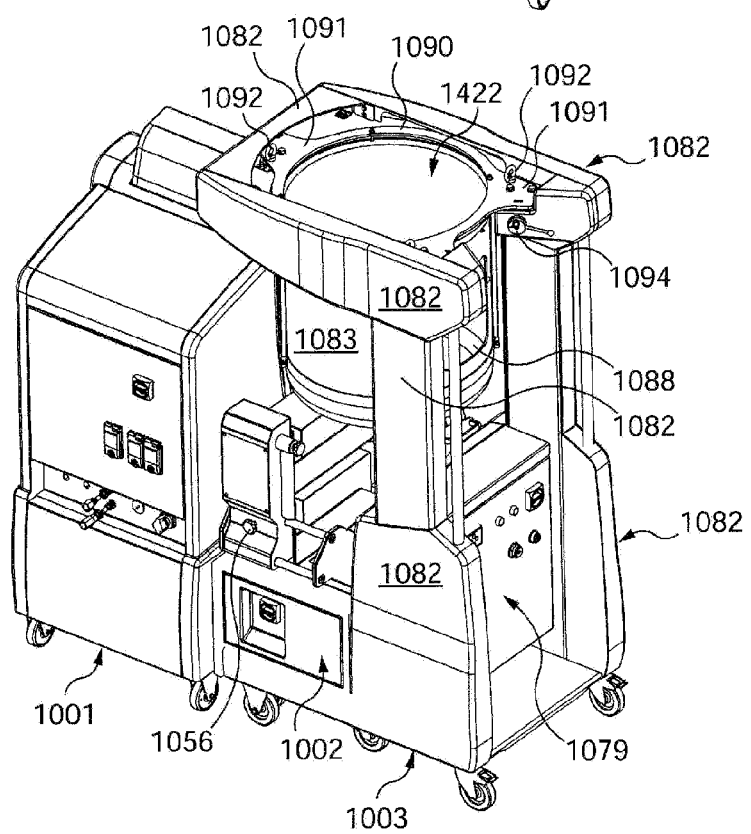

Referring to FIGS. 8 to 10, the same installation with three carts 1001, 1002 and 1003 can be seen, in a nested configuration, that is to say with the first cart 1001 juxtaposed against the second cart 1002, by one of its lateral faces, and the third cart 1003 partially nested in the second cart 1002 by the other of its lateral faces.

Figure 14:
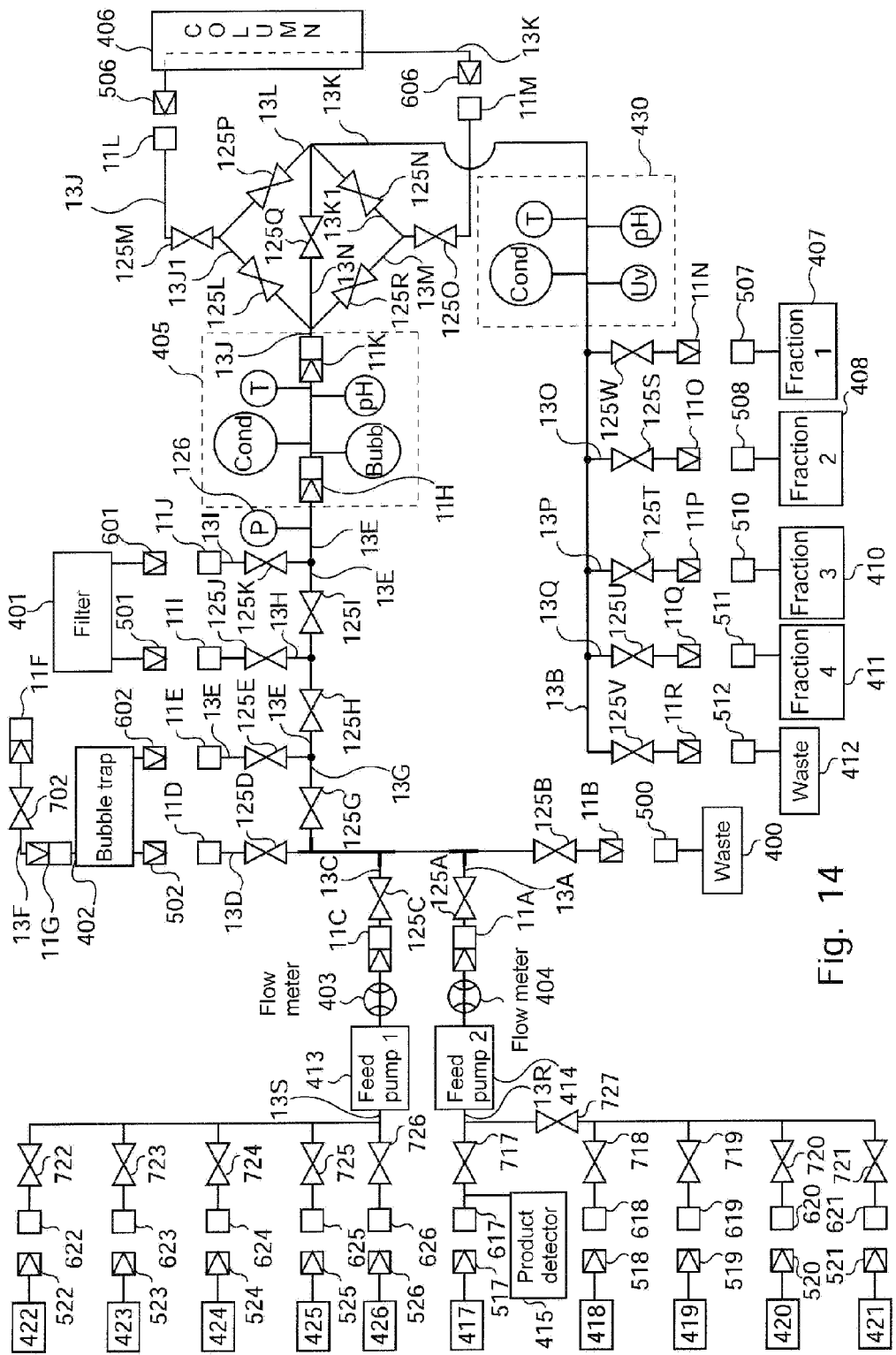
FIG. 14 is a diagrammatic view of the circuit for liquid of the first installation for treatment by chromatography illustrated in FIGS. 1 to 4.

With reference to FIG. 14, a description will first of all be made of the circuit for treating a biological liquid, produced using disposable parts installed on the carts 1, 2 and 3 described above, in the case of treatment by chromatography. The liquid to be treated is initially in a source bag 417 filled with liquid from the previous treatment. This source bag 417 is connectable via a male connector 517 to a conduit 13A. For this, male connector 517 is connected to a female connector 617, which is linked to a feed pump 414 via a conduit 13R. Between that female connector 617 and that pump 414 is situated a product detector 415 as well as a valve 717. At the outlet of the pump 414 there is also a flow meter 404 and then a connector 11A. Containers respectively of buffer liquid 418 to 421 are connectable to that conduit 13A respectively via a male connector 518, 519, 520, 521. These respective male connectors are connectable to corresponding female connectors 618, 619, 620 and 621, which are linked to the feed pump 414 via respective valves 718, 719, 720, 721 and 727.

The sections formed between the various containers and that feed pump are formed by disposable flexible conduits.

The feed pump 414 (here a pump with a disposable head) as well as the respective valves 717 to 721 and 727 enable the liquid to be made to flow to conduit 13A.

The term "conduit" must be understood in the present document as being a portion of tubing connecting two elements of the circuit, it being possible for this portion equally well to comprise a unique tube or on the contrary several tubes, possibly having different diameters, connected in series by a simple connector (not playing any other role here) or sophisticated connector (for example a disposable connector for a pressure sensor (or for a sensor of another physicochemical value)).

A valve 125A is implanted on the conduit 13A near the connector 11A in order to allow or prevent the flow of liquid in that conduit.

Other buffer products are present in respective containers 422 to 426, which are respectively connectable via a male connector 522 to 526 to a conduit 13C via a conduit 13S.

For this the respective male connectors 522 to 526 are connected to respective female connectors 622 to 626, which are connectable to a feed pump 413 via conduit 13S and through respective valves 722 to 726.

At the outlet of the pump 413 there is also a flow meter 403 and then a connector 11C.

A valve 125C is implanted on the conduit 13C near the connector 11C in order to allow or prevent the flow of liquid in the conduit.

The liquid to treat is generally the product coming from the source bag 417. Product detector 415 enables detection of whether liquid is passing in conduit 13A.

As a matter of fact this detector 415 enables the product end to be detected, that is to say when there is no more product flowing but air.

A bubble trap 402 can be linked to a conduit 13E via male connectors 502 and 602 that are connectable to female connectors 11D and 11E.

Valves 125D and 125E enable that bubble trap 402 to be supplied or not.

The bubble trap 402 further comprises an additional valve 702 on a conduit 13F between a connector 11G and a connector 11F which opens to atmosphere.

A filter 401 can be linked to conduit 13E via male connectors 501 and 601 that are respectively connectable to female connectors 11I and 11J.

Valves 125J and 125K enable the liquid to be allowed or prevented from passing through that filter 401.

Valves 125G, 125H and 125I enable the bubble trap 402 and the filter 401 to be avoided, with the valves 125D, 125E, 125J and 125K being shut.

Valve 125H is also a pressure control valve to enable the liquid to go all the way to the bubble trap 402 and to return therefrom.

A pressure sensor 126 is implanted on conduit 13E.

The first cart 1 comprises an instrumentation platform 405 comprising in particular a conductivity sensor, a temperature sensor, a bubble detector and a pH sensor, this platform being disposed ahead of a chromatography column 406.

This platform 405 is connectable by an upstream connector 11H and a downstream connector 11K.

The chromatography column 406 is connectable to a conduit 13J and to a conduit 13K via male connectors 506 and 606, which are connectable to respective female connectors 11L and 11M.

Valves 125L, 125M, 125P, 125N, 125R and 125O enable the flow of liquid to be created in the chromatography column 406.

Valve 125Q enables the chromatography column 406 to be avoided.

The first cart 1 comprises an instrumentation platform 430 comprising in particular a conductivity sensor, a temperature sensor, a pH sensor and a UV sensor, this platform being disposed ahead of collecting containers 407, 408, 410 and 411 and a waste container 412

These collecting containers 407, 408, 410 and 411, as well as the waste container 412, are connectable to a conduit 13K respectively via a female connector 507, 508, 510, 511 and 512, which are connectable to a respective male connector 11N, 11O, 11P, 11Q and 11R.

Valves 125W, 125S, 125T, 125U and 125V enable the flow of liquid to the respective collecting containers and to the waste container 412 to be allowed or prevented.

The operation of this circuit will now be described.

The container 418 of buffer liquid for preparing the column is connected, which buffer liquid passes into the bubble trap 402, into the filter 401, then into the chromatography column 406 until it is collected in the waste container 412.

For this, the valves 718, 727, 125A, 125D, 702, 125E, 125H, 125J, 125K, 125L, 125M, 125O, 125N and 125V are opened, the other valves being closed.

The buffer liquid then passes into conduits 13A, 13D, 13E, 13H, 13I, then also 13E and 13J (including section 13J1), until the chromatography column 406 is reached (passing through the instrumentation platform 405 via the connectors 11H and 11K). The buffer liquid exits from that column 406 and flows into conduit 13K (including a section 13K1) until it reaches conduit 13B to be collected in waste container 412.

Next, the treatment cycle for the source product coming from container 417 is proceeded with, which product passes neither through the bubble trap 402 nor through the filter 401, but passes through the chromatography column 406, and a part (not held back in the column) is collected in the waste container 412.

For this, the valves 717, 125A, 125G, 125H, 125I, 125L, 125M, 125O, 125N and 125V are opened, the other valves being closed.

Thus, the source liquid passes within conduits 13R, 13A, 13D, 13E, and 13J (by section 13J1) until it enters the chromatography column 406. The liquid exits from that column 406 by conduit 13K (and section 13K1) then passes to waste container 412 by conduit 13B.

The product detector 415 detects when there is no more source product in the container 417 (by the appearance of a large air bubble in conduit 13R) and then provides for the pump 414 to be stopped.

Once the source liquid has been treated in the chromatography column 406, a cleaning cycle is proceeded with in which all the source liquid is pushed (so that all this liquid passes into the column) with a buffer liquid contained in container 419 which is connected, which liquid passes through the bubble trap 402, the filter 401, the instrumentation platform 405 and the chromatography column 406 until it is collected in waste container 412.

For this, the valves 719, 727, 125A, 125D, 702, 125E, 125H, 125J, 125K, 125L, 125M, 125O, 125N and 125V are opened, the other valves being closed.

Thus, the buffer liquid passes within conduits 13A, 13D, 13E, 13H, 13I then also 13E and 13J (including section 13J1) until it enters the chromatography column 406. The buffer liquid exits from that column 406 and passes via conduit 13K (including section 13K1) until it reaches waste container 412 by conduit 13B.

An elution cycle (first elution step) is next proceeded with in which elution buffer liquids present in containers 421 and 422 (or from another of the containers 423 to 426) pass through the bubble trap 402, the filter 401, the chromatography column 406 and the platform 430 until they are collected in a container 407 for fraction 1, which is synonymous for a first level of purity of recovered fraction.

For this, the containers 421 and 422 containing the buffer liquid are connected and the mixing of liquids is carried out by virtue of the pumps 413 and 414, with the valves 721, 727, 722 and/or 723 and/or 724 and/or 725 and/or 726, 125A, 125C, 125D, 125E, 125H, 125J, 125K, 125L, 125M, 125O, 125N and 125W opened, the others being closed.

The liquid coming from feed pump 413 passes via conduit 13C and the liquid or liquids from feed pump 414 pass(es) within conduit 13A until the liquids meet in conduit 13D where the mixing thus occurs.

The mixture then passes within conduits 13D, 13E, 13H, 13I and 13J (including section 13J1) until it reaches the chromatography column 406.

The liquid leaves that column 406 bringing with it part of the source product that remained in the column and passes through conduit 13K to reach container 407 for fraction 1 passing via platform 430.

Next, the elution (second step) is continued in which the same mixture passes of buffer liquids from containers 421 and 422 (and/or from another of the containers 423 to 426).

For this, the containers concerned are connected and the mixture is made by virtue of pumps 413 and 414.

Valves 721, 727, 722 and/or 723 and/or 724 and/or 725 and/or 726, and valves 125C, 125A, 125D, 125E, 125H, 125J, 125K, 125L, 125M, 125O, 125N et 125S are opened, the other valves being closed.

Thus the mixture obtained passes through the bubble trap 402, the filter 401, the instrumentation platform 405 then the chromatography column 406 and the platform 430 until it is collected in the container 408 for fraction 2, which is a synonymous for a second level of purity of recovered fraction, superior to the first level.

The liquid coming from feed pump 413 passes via conduit 13C and the liquid or liquids from feed pump 414 pass(es) within conduit 13A until the liquids meet in conduit 13D where the mixing thus occurs.

The mixture then passes within conduits 13D, 13E, 13H, 13I and 13J (including section 13J1) until it reaches the chromatography column 406.

The liquid leaves that column 406 bringing with it another part of the source product that remained in the column and passes through conduit 13K to reach container 408 for fraction 2 via a conduit 13O.

Other steps may be carried out with regard to this fraction 2 of collected product, such as an adjustment of pH.

Lastly, in a regenerating cycle of the chromatography column 406, a regenerating buffer product from container 420 passes into the bubble trap 402, into the filter 401, and into the chromatography column 406, from the bottom, until it is collected in the waste container 412.

For this, container 420 is connected and the valves 720, 727, 125A, 125D, 125E, 125H, 125J, 125K, 125R, 125O, 125M, 125P and 125V are opened, the other valves being closed.

This regeneration liquid thus passes into conduits 13A, 13D, 13E, 13H, 13I then also 13E, 13J, 13M (the liquid does not pass into conduit 13J1), and conduit 13K until the chromatography column 406 is reached (the liquid does not pass into the chromatography column from the top) at connector 11M, then passes into conduit 13J until reaching the end 13J2 of section 13J1, then 13L, then 13K (the liquid not passing into sections 13J1 and 13K1) until reaching the waste container 412 via conduit 13B.

It is possible to drain the circuit (for example before changing source product) between valves 717 to 727 and the pumps 413 and 414 by opening those valves as well as valve 125B, the other valves being closed, and by connecting connector 500 of waste container 400 to connector 11B.

For each step described above, it is possible to avoid the bubble trap 402 by opening valve 125G and by closing valves 125D and 125E (the liquid does not pass into conduit 13D) so as to make the liquid pass via conduit 13G.

Furthermore, it is also possible to avoid filter 401 by opening valve 125I and by closing valves 125J and 125K (the liquid does not flow into conduits 13H and 13I).

The installation that uses the circuit described above is described next with reference to FIGS. 1 to 6.

The first cart 1 is of generally parallelepiped form.

This first cart 1 comprises a base 10 having a first lateral face 11, a second lateral face 12 which is an opposite face to the first lateral face 11, a front face 14 meeting the first and second lateral faces 11 and 12, and a back face 15 which is an opposite face to the front face 14 and which meets the first and second lateral faces 11 and 12.

The first cart 1 further comprises a circuit portion 16 provided with a press 17 and a bag 18, which comprises the connectors 11A to 11R described above for liquid and a liquid conveying network 19 between those connectors 11A-R whose conduits 13A to 13Q are described above, at least in part. Certain conduits are formed in entirety in the bag 18 and for others only one or more sections, with other sections of these latter conduits being external to the bag 18, these sections here being referred to as conduit extensions below.

Valves 125A to 125W are implanted in shell 20, as well as the pressure sensor 126.

The press 17 comprises two shells 20 and 21 each formed from a solid block of rigid material.

Here, shell 20 is of polyoxymethylene (POM), also called acetal, and is approximately 175 mm thick, and shell 21 is of polymethyl methacrylate or Plexiglas™ (PMMA), and is approximately 50 mm thick. They are each of generally parallelepiped form.

The shell 20 is mounted on the front face 14 of the base 10.

The first cart 1 further comprises a door 22 hinged to the base 10.

The shell 21 is mounted in that door 22.

The first cart 1 has a closed door position in which the door 22 is closed and covers the shell 20, and another position (not shown) in which the bag 18 is carried only by the shell 20.

In this other position, the shell 21 is away from the shell 20.

In the closed door position, the bag 18 is inserted between the two shells 20 and 21.

The first cart 1 is provided, at the bottom, with a closed bay 23 intended to receive one or more tanks adapted to receive the filter 401.

This bay 23 is closed by a sliding panel disposed on the front face 14 of the first cart 1, which panel is adapted to be moved in translation downwardly then towards the back of the first cart 1 (see the arrows in FIG. 1) so as to insert and withdraw the filter 401.

A control panel 24 is arranged at the top of the front face 14 of the first cart 1, at a height enabling an operator to use it.

This control panel 24 is provided with a graphical touch interface enabling the biological liquid treatment process to be controlled and operated.

In order to make it easier to move, the first cart 1 is mounted on four wheels 25 of which two, situated under the front face 14 of the first cart, comprise a brake 26, and cart 1 furthermore having two handles 27 on respective opposite sides of the front face 14, in the vicinity of the respective lateral faces 11 and 12.

The first cart 1 comprises, at its front face 14, an inclined chassis on which shell 20 is hooked via L-shaped hooking claws.

A support plate 28 is fastened to the right side of the chassis of the base 10 at the location of two fixing heads 29 provided on that chassis.

Two instrumentation platforms 405 and 430 (in fact just forming a single overall platform here) are fastened to that support plate 28.

Instruments necessary for the treatment (described earlier) are mounted on this overall platform 405, 430. Represented here are two sensors of conductivity and temperature, two pH sensors, which are associated with a respective control interface for conductivity and pH, and a UV sensor associated with an interface.

The base 10 of the first cart 1 further comprises three devices 30 for locking the door 22 in its closed door position. These devices 30 are of ball-lock pin device operating as a pneumatic jack.

The door 20 comprises a stainless steel frame 31 having a generally rectangular outline, which frame surrounds a pane of glass 32 having a thickness of approximately 4 mm.

The first cart 1 further comprises a single hinge 33 hinging door 22 to base 10, which hinge 33 comprises a first hinge portion 34 fastened to the upper right corner of frame 31 of door 22, and a second hinge portion (not shown) fastened to the lateral face 11 of base 2 of the first cart 1.

In the frame 31 of door 22 a system is provided (not shown) for locking shell 21 in door 22 which is supplied with power by that hinge 33.

In the closed door position, the rotational axis about which the first hinge portion 34 of the door 22 pivots is offset relative to a parting surface formed between the shells 20 and 21 when they clamp the bag 18 between them.

This axial offset towards the front of the first cart 1 enables lateral clearances to be formed between the door 22 and the base 10 at the outer perimeter of the door 22 (FIG. 1), which facilitates the access to the connectors 11A-R of the bag 18.

The shells 20 and 21 each have a flat reference surface and a plurality of shaping channels recessed relative to that reference surface and which face a corresponding shaping channel. Generally, these surfaces have similar dimensions and the arrangement of the shaping channels of shell 20 is the mirror image of the set of the shaping channels of shell 21. These shaping channels are of semi-elliptical cross-section, and may be applied against each other with the channels in register with each other to delimit a network of cavities which are each generally tubular.

Shell 21 is provided with positioning holes (not shown) for positioning bag 18, which are arranged facing positioning apertures (not shown) of bag 18 in the closed door position. Furthermore, shell 21 is provided with positioning holes (not shown) for positioning the door 22 in the closed door position, which are arranged facing positioning apertures (not shown) of bag 18 in the closed door position. Shell 21 further comprises holes (not shown) for locking together the shells 20 and 21, which are situated at the locations where there are the most channels serving for the formation of the conduits 13A-Q, since it is at these locations that the force of pressure is highest during the treatment, and are arranged facing locking apertures (not shown) of bag 18, in the closed door position.

Shell 20 comprises hooking studs (not shown) adapted to pass through the positioning apertures of bag 18 for the latter to be hung on shell 20 and to be inserted into the positioning holes of shell 21 in the closed door position. Shell 20 comprises positioning dowels (not shown) for positioning door 22, which are adapted to pass through the apertures of bag 18 and to be inserted in the positioning holes of shell 21. Shell 20 further comprises locking holes (not shown) which are situated at the locations where there are the most grooves serving for the formation of the conduits 13A-Q, and which are arranged facing the locking holes passing through bag 18 when the latter is disposed on shell 20, and also arranged facing locking holes corresponding to shell 21 in the closed door position. These locking holes of the shell 20 are passed through by pneumatic ball-lock pins (not shown) (operating as pneumatic jacks) for the locking together of the shells 20 and 21 when the door 22 is in its closed position, and for the clamping of the bag 18 in the circuit portion 19.

In addition to the shells 20 and 21, the first cart 1 comprises, implanted here on the back of shell 20 (FIG. 3), instruments necessary for the treatment of the biological liquid (not visible), such as the pinch valves 125A to 125W (FIG. 14) comprising actuators for pinching a corresponding conduit 13A-Q so as to prevent or allow the passage of liquid in that conduit 13A-Q, a pressure sensor, a pneumatic distributor and means for control, operation (in particular an electrical selector), and communication (in particular a network plug) for communicating for example with the second cart 2 and the biological liquid feed unit 3.

The power supply is thus electrical (for power and control) and pneumatic.

The bag 18 comprises two flexible films (not shown) connected to each other by a seal delimiting a closed contour, and the connectors 11A-R of the conveying network 19. The conduits 13A-Q are formed on passage of a liquid.

The bubble trap 402 (FIG. 4) is here represented "floating" but in reality it is advantageously mounted on the first cart 1.

The pump cart 2, referred to as second cart, is of generally parallelepiped form, its interior being hollowed out to allow the nesting of the biological liquid feed unit 3.

This second cart 2 has a first lateral face 40, a second lateral face 41 which is an opposite face to the first lateral face 40, a front face 42 meeting the two lateral faces 40 and 41, and a back face 43 which is an opposite face to the front face 42 and also meets the two lateral faces 40 and 41.

The front face 42 and the back face 43 each have a recess 46 at the base of those faces 42 and 43, which recesses 46 are adapted to receive feet of another cart (see the following embodiment).

To enable it to be easily moved, the second cart 2 is mounted on four wheels, of which two, which are situated adjacent the first lateral face 40, further comprise brakes 48.

The second cart 2 comprises a first removable panel 51 on the first lateral face 40 to cover the internal space, and a second removable panel (not shown) on the second lateral face 41 also to cover that internal space.

The shape of the second removable panel is adapted to conform to the shape of the base of a panel of the first lateral face 11 of the first cart 1 for them to be perfectly juxtaposed (almost nested).

The second cart 2 has furthermore an upper face 44 represented in the form of a plate, on which are fastened two arms 45 extending upwardly and towards the back of the second cart 2.

One of the arms 45 is disposed in the vicinity of the first lateral face 40, and the other of the arms 45 is disposed in the vicinity of the second lateral face 41, with its two arms 45 facing each other.

The two arms 45 are spaced apart by two slide rods 49 (FIGS. 3 to 6) which are furthermore each rigidly attached to each of the two arms 45.

The second cart 2 further comprises a pump support 50 which is movably (slidingly) mounted on the slide rods 49.

This pump support 50 is thus movable in translation in a direction going from the first lateral face 40 towards the second lateral face 41 of the second cart 2, and in particular between the two arms 45, which thus form abutments for the pump support 50.

The pump support 50 comprises a vertical block 52 mounted on the rods 49 and two stainless steel receptacles 53 each adapted to bear a pump 413, 414.

On a back wall 55, the vertical block 52 has an operating handles 56 for locking block 52 against movement in translation on rods 49 in order to fix the support 50 in particular for performing the treatment.

On a front wall 54, vertical block 52 furthermore has dowels 57 for positioning and hooking on of the receptacles 53.

Three dowels 57 provided at a location of predetermined height on the front wall 54 enable a receptacle 53 to be hooked on, and the front wall 54 here comprises four locations of predetermined height, of which two enable hooking on of the two receptacles 53 for the respective pumps 413 and 414 for the chromatography treatment.

Here, the locations at predetermined height are superposed to enable the two pumps 413 and 414 to be mounted in superposed manner on the second cart 2. Furthermore, vertical block 50 has electrical power supply means (not shown) to which the pumps 413 and 414 are connected for their actuation.

Each receptacle 53 is in the form of a tank with four sides, with the bottom side 58 being provided with three apertures 59 each adapted to receive a dowel 57 for the hooking on of receptacle 53.

Each receptacle 53 furthermore has a cut-out 60 on the front, which is formed by an incision on each of the lateral and front sides (not shown).

The front side furthermore has a circular incision for the passage of the head of the respective pump 413, 414 which is disposable.

The second cart 2 also comprises a handle 61 which is movable between a withdrawn position (FIGS. 5 and 6) and an extended position (not shown) in which that handle 61 is then in a position better adapted for moving the second cart 2.

To move the handle 61 from its withdrawn position to its extended position, it suffices to undo an operating handle 62, then to pivot the handle 61 upwardly to reach a substantially horizontal position, then to do up the handle 62 once again, and conversely if its is wished to pass from the extended position to the withdrawn position.

Handle 61 is furthermore removable by fully undoing operating handle 62, as is shown in FIGS. 1 to 4.

In FIG. 4, the flow meters 403 and 404 can be seen, which here are shown "floating" but which in reality are advantageously mounted on the second cart 2. On its back face 43, second cart 2 further comprises (FIG. 3) pneumatic and electrical power supply means to actuate pumps 413 and 414, and controlling and operating means (such as switches) (not shown).

The biological liquid feed unit 3 comprises a base 64 adapted to be nestingly mounted in the internal space of the second cart 2, that base 64 resting on a bottom wall (not shown) of that second cart 2.

Unit 3 further comprises a distributor block 65 of parallelepiped form mounted on base 64.

The distributor 65 has a first lateral face 66 and a second lateral face 67 which is an opposite face to the first lateral face 66, which second lateral face 67 faces the second cart 2 when they are nested.

Unit 3 furthermore has a front face 68 meeting the two lateral faces 66 and 67, and a back face 69 which is an opposite face to the front face 68 also meeting the lateral faces 66 and 67.

Valves 717 to 726 described earlier are provided on the first lateral face 66, as well as the product detector 415.

On each of the front 68 and back 69 faces there are provided two handles 70 which make it possible to lift the feed unit 3, and to move the assembly formed by the feed unit 3 and the second cart 2 when they are nested (handle 61 of second cart 2 then being removed).

On its back face 69, the distributor 65 further comprises (FIG. 3) pneumatic and electrical power supply means to actuate valves 717 to 726, and controlling and operating means (such as switches) (not shown).

With reference to FIG. 4, a description will now be given of the assembly of the two carts 1 and 2 and of the biological liquid feed unit 3 as well as of the connection of certain conduits of the installation for the chromatography treatment.

Of course, the assembly may be made in a different order to that which will be described.

In a first phase, at least one operator grasps the biological liquid feed unit 3 manually (or with the aid of an electric winch) via the handles 70 of the distributor 65 to nest its base 64 into the internal space of the second cart 2, after having removed the first panel 51 of the second cart 2.

Next, the operator removes the second panel of the second cart 2 to make the electrical and/or pneumatic connections between the second cart 2 and the feed unit 3.

Next, the operator installs pumps 413 and 414 on a respective receptacle 53 at a location of predetermined height on the pump support 50. Here pump 413 is above pump 414, the pumps being superposed.

The operator installs conduit 13R by connecting the head of pump 414 to one of the containers 417 to 421, via one of the respective valves 717 to 721. If conduit 13R links pump 414 to the source product container 417, that conduit 13R furthermore passes via the product detector 415.

The operator installs conduit 13S by connecting it first of all to the pump head 413, via at least one of the respective valves 722 to 727, then subsequently to one of the containers 422 to 426 (not visible in FIG. 4)

Next the operator moves the second cart 2 towards the first cart 1 until the second lateral face 41 of the second cart 2 is juxtaposed against the first lateral face 11 of the first cart.

Beforehand, the operator has installed the modules of the first cart 1, that is to say that he has placed shell 20 on base 10, shell 21 in door 22 and bag 18 on shell 20, naturally after having placed the door 22 in the position which is not the closed door position, then has placed the door 22 in the closed door position 22.

Next the operator connects the flow meter 404 to the pump head 414, and also to the connector 11A of bag 18 by installing an extension to conduit 13A.

It is to be noted that the location of predetermined height of the pump support 50 on the vertical block 52 is configured such that the head of the pump 414 faces connector 11A of bag 18, and consequently such that the extension of conduit 13A is substantially straight.

Next the operator connects the flow meter 403 to the pump head 413, and also to the connector 11C of bag 18 by installing an extension to conduit 13C.

It is to be noted that for the installation of conduits 13A and 13C, the pump support 50 may be situated at any point on the slide rods 49, but is preferable for it to be positioned at a predetermined transverse first location (transverse relative to the location in height) in order to move it as far away as possible from the first cart 1 to have sufficient space to install the extensions to conduits 13A and 13C.

The operator next locks the pump support 50 at that predetermined transverse first location which is the furthest from the first cart 1 using the locking handle 56.

As the space is sufficient between pumps 413 and 414 and the first cart 1, the operator installs the bubble trap 402, interposed between the second cart 2 and the first cart 1, and connects it, by one of those connectors to connector 11G of the bag by installing an extension to conduit 13F, then by another of those connectors to connector 11E of bag 18 by installing a first extension to conduit 13E, and by still another of those connectors to connector 11D of bag 18 by installing an extension to conduit 13D.

Next, the operator connects the instruments by installing in particular a second extension to conduit 13E between connector 11H of bag 18 and instruments, a first extension of conduit 13J between connector 11K of bag 18 and instruments, and a first extension of conduit 13K between a connector 11M of bag 18 and instruments.

The operator also connects filter 401 to connectors 11I and 11J of bag 18 by installing extensions to respective conduits 13H and 13I.

The operator furthermore connects the chromatography column 406, which is generally placed on the floor by installing a second extension to conduit 13J between connector 11L of bag 18 and connector 506 of column 406, and a second extension of conduit 13K between connector 606 of that column 406 and instruments.

Other conduits (not shown in FIG. 4) are added by the operator, and in particular the conduits to the fraction containers 407, 408, 410 and 411 and the waste containers 412 and 400.

The installation is thus ready for the chromatography treatment described earlier.

Figure 15:
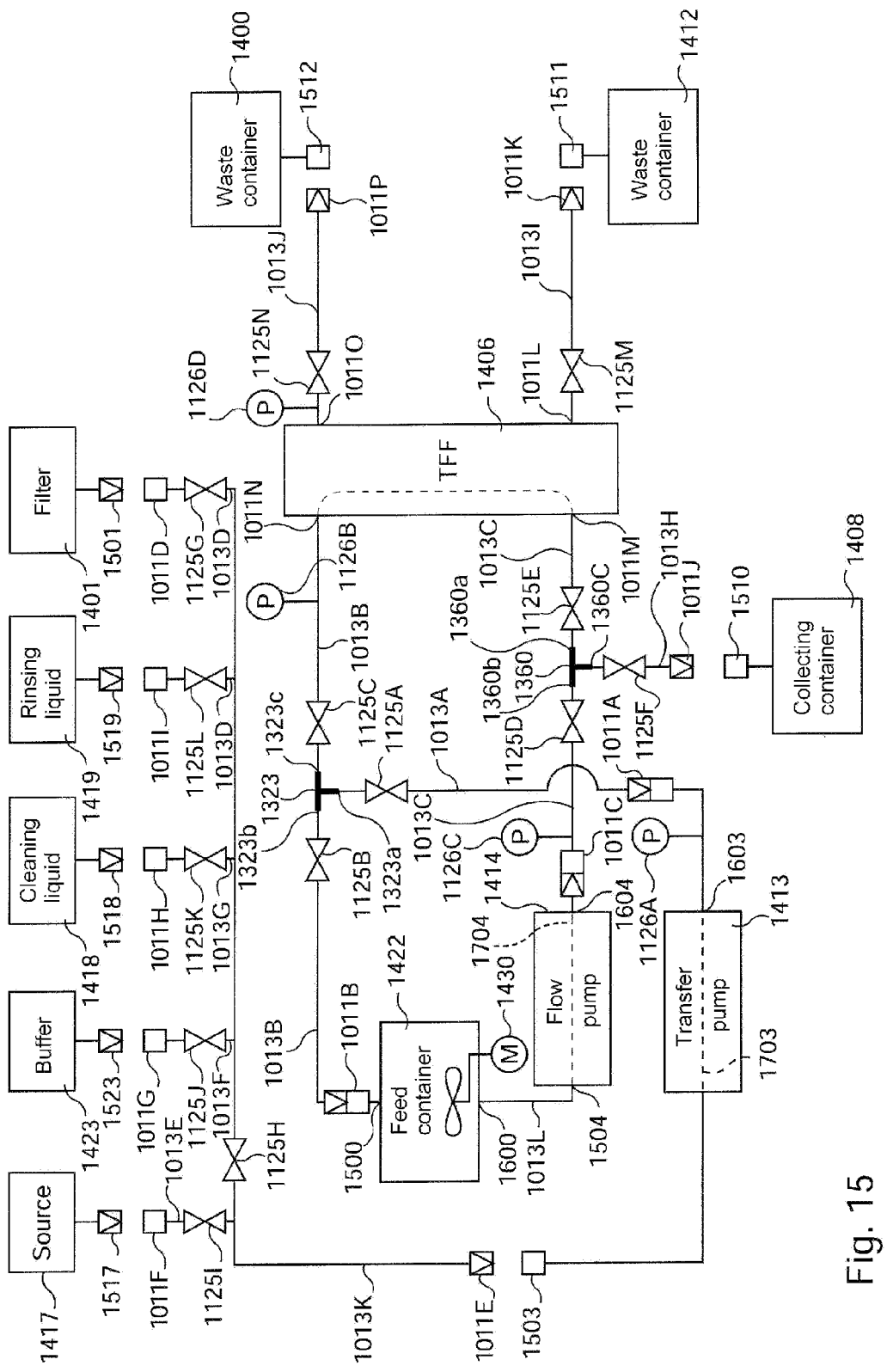
FIG. 15 is a diagrammatic view of the circuit for liquid of the second installation for treatment by tangential filtration illustrated in FIGS. 7 to 10.

With reference to FIG. 15, a description will now be given of the circuit for treating a biological liquid, also produced using disposable parts installed on the carts 1001, 1002 and 1003 described briefly above, in the case of treatment by tangential filtration.

Generally, the same reference numbers increased by 1000 are used for similar parts.

The liquid to be treated is initially in a source bag 1417 filled with liquid from the previous treatment. This source bag 1417 is connectable via a male connector 1517 to a transfer conduit 1013E which extends between a female connector 1011F and another female connector 1011E, that transfer conduit 1013E being connectable via its female connector 1011E, to a transfer section, which is connectable to a transfer conduit 1013A which extends between a female connector 1011A to a first aperture 1323a of a T-shaped branching connector T1323 (formed by the crossing of conduits 10138 and 1013C).

This transfer section comprises disposable flexible conduits, a transfer pump 1413 to make the liquid circulate (here a pump with a disposable head) and two valves 1125A and 1125I.

The disposable head of pump 1413 has a first inlet/outlet point 1703 and a second inlet/outlet point 1603 such that the liquid passes through it.

The valve 1125A is implanted on the conduit 1013A near the branching connector 1323 in order to allow or prevent the flow of liquid in the conduit.

The transfer section also comprises a connector for a pressure sensor 1126A. The valve 1125I is implanted on the conduit 1013E close to the female connector 1011F.

The operator has the possibility of linking other bags 1417, 1418, 1419 and a filter 1401 to a transfer conduit 1013K meeting the conduit 1013E, via respective male connectors 1517, 1518, 1519 and 1515 which may connect into a respective female connector 1011G, 1011H, 1011I and 1011D.

These bags 1417, 1418 and 1419 respectively contain a buffer liquid (saline solution), a cleaning liquid (sodium hydroxide) and a rinsing liquid (water) to manage the state of cleanliness of the circuit or to push the treated liquid towards the components which perform the treatment or towards the collecting container, and the filter 1401 is an air filter.

The conduit 1013B has two sections, one of which is for filling (between a connector 1011A and the intersection of the conduit 1013B and the conduit 1013A) and the other is for filtration (between a connector 1011N and the intersection of the conduit 1013B and the conduit 1013A), which sections extend respectively from a second aperture 1323b and from a third aperture 1323c of the branching connector 1323.

The filling section which meets a connector 1011B then an inlet/outlet aperture 1500 of a feed container 1422, comprises a valve 1125B implanted close to the branching connector 1323.

This feed container 1422 is formed by a flexible disposable bag.

A stir bar 1430 actuated by an electromagnetic drive 1425, is disposed in the container 1422 in order to make the liquid contained therein homogenous.

The conduit 1013C has two sections, one of which forms a filtration section which joins a first aperture 1360a of a T-shaped branching connector 1360, and comprises a connector for a pressure sensor 1126C, two isolation valves 1125D and 1125E and a tangential filter 1406, and the other a feed section.

The conduit 1013B links the third aperture 1323c of branching connector 1323 to a first inlet/outlet aperture of the filter 1406 via the connector 1011N.

The conduit 1013C links a second inlet/outlet aperture of the filter 1406 to the first aperture 1360a of the branching connector 1360 via the connector 1011M. The measurement made by the pressure sensor 1126B makes it possible to know the functional state of the tangential filter 1406.

A valve 1125C is implanted on conduit 1013B close to the branching connector 1323, whereas a valve 1125E is implanted on the conduit 1013C close to the branching connector 1360.

A feed section and a collecting section respectively extend from a second aperture 1360b and from a third aperture 1360c of the branching connector 1360.

The feed section joins an outlet aperture 1600 of the feed container 1422 via a conduit 1013L disposed between the flow pump 1414 and that aperture 1600. It comprises a disposable flexible conduit, a flow pump 1414 to make the liquid flow (here, a pump with a disposable head), a valve 1125D implanted on the conduit 1013C close to the branching connector 1360, and a connector for the pressure sensor 1126C inserted in series in conduit 1013C.

The feed section is formed here by the portion 1704 representing the disposable head of pump 1414, which head has an inlet point 1504 and an outlet point 1604.

The feed section further comprises a section of the conduit 1013C situated between the valve 1125D and the connector 1011C connected to the flow pump 1414.

The collecting section joins a female connector 1011J. It comprises solely a conduit 1013H and an isolation valve 1125F implanted on conduit 1013H close to the branching connector 1360.

Depending on the operations carried out, the connector 1011J may be connected either to a male connector 1511 of a waste container 1412, or to the male connector 1510 of a collecting container 1408.

The tangential filtration treatment circuit also comprises two conduits 1013J and 1013I for conveying the filtrate which respectively extend from outlet points of the filter 1406 via the respective connectors 1011I and 1011L, those conduits 1013J and 1013I being connected via the respective connectors 1011P and 1011K to the respective male connectors 1512 and 1511 of the respective collecting containers 1400 and 1412. It is possible to interpose a flow meter (not shown) such that the volume and the rate of flow of the filtrate recovered at the outlet of the filter 1406 can be determined.

Valves 1125N and 1125M are respectively implanted in the respective conduits 1013J and 1013I, close to the filter 1406, and a connector for a pressure sensor 1126D is implanted in the conduit 1013J, between the valve 1125N and the filter 1406.

The measurement made by the pressure sensor 1126D, in conjunction with the measurement made by the pressure sensor 1126B, enables the functional state of the tangential filter 1406 to be checked precisely.

The operation of this circuit will now be described.

The valves 1125C, 1125D and 1125F are closed in order to prevent any flow of liquid in the filtration and collecting sections, the other valves being open.

The source bag 1417 is joined to the transfer section by connecting the male connector 1517 to the female connector 1011F and by connecting the male connector 1503 to the female connector 1011E.

The liquid to treat is next sucked from the source bag 1417 by the transfer pump 1413 and is conveyed to the feed container 1422 via the transfer section 1013A and filling section 1013B.

Once the transfer has been carried out, the valves 1125E and 1125D are opened, the liquid to treat is made to flow by the actuation of the flow pump 1414, in the sub-circuit formed by the feed section. After the passage of the liquid into tangential filter 1406, the retentate comes back to feed container 1422 whereas the filtrate is evacuated via conduits 1013J and 1013I to be collected in waste containers 1400 and 1412.

The operation of making the liquid to treat flow into filter 1406 is continued until the liquid attains a first desired concentration.

After this first concentrating step, bag 1423 containing the buffer liquid is connected via connector 1523 to connector 1011G. This buffer liquid is then introduced into transfer section 1013A thanks to transfer pump 1413 in order to push the liquid to treat towards conduit 1013B such that the entirety of that liquid can be filtered and retrieved. Conduit 1013A is next isolated from conduit 1013B by closing valve 1125A.

Once the transfer has been carried out, valves 1125E and 1125D are opened again, and the liquid to treat is made to flow by the actuation of flow pump 1414, in the sub-circuit formed by the feed section. After the passage of the liquid into tangential filter 1406, the retentate comes back to feed container 1422 whereas the filtrate is evacuated via conduits 1013J and 1013I to be collected in waste containers 1400 and 1412.

The operation of making the liquid to treat flow into filter 1406 is continued until the liquid attains a second desired concentration.

The collection of the filtered liquid is then carried out in two successive sub-steps.

The first sub-step consists of recovering the filtered liquid contained in the filtration section formed by a section of conduit 1013B and in the filter 1406.

For this, valve 1125B is closed whereas valve 1125A is opened so as to place the transfer and filtration sections in communication, and to isolate them from the filling section formed by the other section of conduit 1013B.

In parallel, valve 1125D is closed whereas valves 1125F and 1125E are opened so as to place in communication the filtration section formed by a section of conduit 1013B and the collecting section formed by conduit 1013H, and to isolate them from the feed section.

Female connector 1011J is connected to male connector 1510 of collecting container 1408.

Buffer liquid is then conveyed into the transfer section (conduit 1013A) by virtue of transfer pump 1413 in order to transfer, via the collecting section (conduit 1013H), the buffer liquid, and thereby the remainder of the filtered liquid contained in the filtration section (portion of conduit 1013B and conduit 1013C) and filter 1406 to collecting container 1408.

The second sub-step consists of collecting the filtered liquid contained in the filling (portion of conduit 013B) and feed (conduit 1013C) sections, and in the feed container 1422.

For this, the valve 1125C is closed whereas the valve 1125B is opened so as to place in communication the transfer (conduit 1013A) and filling (portion of conduit 1013B) sections, and to isolate them from the filtration section (other portion of conduit 1013B and conduit 1013C).

In parallel, valve 1125E is closed whereas valve 1125D is opened so as to place in communication the feed (section of conduit 1013C) and collecting (conduit 1013H) sections, and to isolate them from the filtration section (other section of conduit 1013B and other section of conduit 1013C).

Buffer liquid is next conveyed into the transfer section (conduit 1013A) by virtue of transfer pump 1413 in order to transfer the filtered liquid contained in the filling section (other section of conduit 1013B) into feed container 1422.

The flow pump 1414 next enables that liquid to be brought from container 1422 to collecting container 1408, via the feed and collecting sections.

The installation that uses the circuit described above is described next with reference to FIGS. 7 to 13.

In contrast to conveying network cart 1, conveying network cart 1001, also referred to as first cart, comprises a circuit portion 1016 comprising a bag 1018 which is different from bag 18, that bag 1018 being provided with connectors 1011A to 1011N and with a network 1019 for conveying liquid between those connectors 1011A to 1011N including conduits 1013A to 1013K described above for the treatment by tangential filtration.

Valves 1125A to 1125N are implanted in shell 1020, as well as pressure sensors 1126A to 1126D.

Thus, support plate 1028 fastened onto base 1010 of the first cart 1001 solely bears the tangential filter 1406 via a platform 1075.

In the same way as for first cart 1, first cart 1001 comprises a transparent shell 1021, and a movable door 1022 having a pane of glass, shell 1021 being mounted in door 1022.

In contrast to pump cart 2, pump cart 1002, also referred to as second cart, has two pumps 1413 and 1414 disposed at locations of predetermined height on vertical block 1052 of pump support 1050 that are different from the locations of predetermined height on which are disposed the two pumps 413 and 414 on the pump support 50 in FIGS. 1 to 4.

More particularly, receptacle 1053 which receives pump 1413 is mounted at the lowest location of predetermined height on vertical block 1052, and receptacle 1053 which receives pump 1414 is mounted at an intermediate location of predetermined height on vertical block 1052, in order for pump 1414 to be above pump 1413.

Biological liquid feed unit 1003, in contrast to biological liquid feed unit 3, takes the form of a generally parallelepiped cart, here called third cart.

It is also to be noted that the third cart 1003 extends over a height on the ground that is much greater than that of second cart 1002, and over a height substantially close to that of the first cart 1001.

In order to facilitate its movement in the treatment zone, third cart 1003 is mounted on wheels 1076, of which two have a brake 1077, and the third cart 1003 has two handles 1078 which project from a first lateral face 1079. This cart is hollow in order to receive certain parts of the circuit, and partly open at its front face 1080 and at its lateral faces 1079 and 1099 in order to simplify the connection operations.

This third cart 1003 comprises:

an inner metal chassis 1081 (FIGS. 11 to 13) partly covered by flat panels 1082;

a plastic feed tank 1083 for receiving the feed container 1422;

the electromagnetic drive 1430 (FIG. 10);

an infrared temperature probe (not shown);

command means 1084 for controlling the speed of the electric motor of the electromagnetic drive 1430; and verification means 1085 for displaying the values measured in the circuit within tank 1083 (in particular the temperature of the liquid within the feed container 1422 and the weight of tank 1083).

Tank 1083 comprises a cylindrical lateral wall 1086 of which one of the ends is extended by a frusto-conical bottom wall 1087 provided with an oblong opening (not shown) for the passage of the apertures 1500 and 1600 of the flexible and disposable feed container 1422, and two other circular openings (not shown) for the cooperation with the electromagnetic drive 1430 and the temperature probe (not shown).

At the location of the first literal face 1079, the cylindrical lateral wall 1086 has an opening 1088 (FIG. 9) in the form of a door for the insertion of the feed container 1422 into the plastic tank 1083.

This opening 1088 is of substantially rectangular shape with a length of approximately 250 mm and a height of approximately 350 mm.

The bottom of the internal metal chassis 1081 of the third cart 1003 has two feet 1089 which form a fork, its feet 1089 being adapted to be inserted into the recesses 1046 of the second cart 1002 for them to be nested.

The electromagnetic drive 1430 is directly fastened to the plastic tank 1083.

As can be seen in FIG. 9, the third cart 1003 also comprises electrical power supply means on its first lateral face 1079 such that this third cart is adapted to operate autonomously, for example when it is dissociated from the rest of the installation, in particular for stirring the biological liquid in feed container 1422 and/or for taking temperature measurements.

Tank 1083 is mounted on a circular frame 1090 having three lugs 1091, each comprising an eye 1092 for the deposit and removal of tank 1083 in the third cart 1003, using for example an electric winch.

This circular frame is linked to the internal metal chassis 1081 via partly visible weight gauges 1093 interposed between each lug 1091 of the circular frame 1090 bearing the tank 1083 and the internal metal frame 1081 of the third cart 1003, which weight gauges 1093 enable the mass of the tank 1083 to be precisely determined.

Weight receiving members 1094 of tank 1083 are interposed between the circular frame 1090 and the internal chassis 1081 at the location of each weight gauge 1093.

These members 1094 comprise a crank 1095 linked to a cam 1096 (FIGS. 11 to 13), that cam 1096 being adapted to be in a horizontal position when the crank 1095 adopts a resting configuration, and, the case arising, the tank 1083 is resting on the weight gauges 1093, cam 1087 also being adapted to be in a vertical position in which it separates circular frame 1090 from the internal chassis 1081 when the operating lever 1095 adopts a working configuration, and, the case arising, frame 1090, and consequently tank 1083, are not resting on the weight gauges 1093.

To pass from the resting configuration to the working configuration, the operator has to press on a locking push button 1097 in order to pivot crank 1095 so as to rotationally drive the cam to reach its vertical position 1096.

A description will now be given, with reference to FIG. 10, of the assembly of the three carts 1001, 1002 and 1003 as well as of the connection of certain conduits of the installation for the treatment by tangential filtration.

Of course, the assembly may be made in a different order to that which will be described.

In a first phase, the operator installs pumps 1413 and 1414 on a respective receptacle 1053 at a location of predetermined height on the pump support 1050. Here pump 1414 is above pump 1413, the pumps being superposed.

Next, the operator slides the pump support 1050 fully towards the second lateral face 1041 of the second cart 1002 until it abuts arm 1045.

Next, the operator grasps the third cart 1003 via handles 1078 to nest its feet 1089 in the respective recesses 1046 of the second cart 1002.

Next, the operator moves the assembly formed by the second cart 1002 and the third cart 1003 towards the first cart 1001 until the second lateral face 1041 of the second cart is juxtaposed against the first lateral face 1011 of the first cart. Beforehand, the operator has installed the modules of the first cart 1001, that is to say that he has placed shell 1020 on base 1010, shell 1021 in door 1022 and bag 18 on shell 1020, naturally after having placed the door 1022 in the position which is not the closed door position, then has placed the door 1022 in the closed door position 1022.

It is to be noted that the location of predetermined height on vertical block 1052 of pump support 1050 is configured such that the head of pump 1414 faces connector 1011C, and consequently such that conduit 1013C is substantially straight between pump 1414 and the rest of conduit 1013C at the bag 1018 of the first cart 1001.

The operator then connects pump 1413 to connector 11A of bag 1018 by installing an extension of conduit 1013A.

It is to be noted that for the installation of conduits 1013C and 1013A, the pump support 1050 is at a predetermined transverse location situated as close as possible to the first cart 1001 and therefore is situated on the slide rods 1049 near the second lateral face 1041 of the second cart 1002.

The operator next locks the pump support 1050 at that predetermined transverse location which is the closest to the first cart 1001 using the locking handle 1056.

The operator installs conduit 1013K by connecting the head of pump 1413 to connector 11E of bag 1018.

The operator installs conduit 1013L by connecting the head of pump 1414 to the feed container 1422 situated in tank 1083.

The operator then installs an extension of conduit 1013B between that feed container 1422 and connector 11B of bag 1018.

The operator next connects tangential filter 1406 via its four inlets/outlets by installing an extension of conduit 1013I between connector 1011L of bag 1018 and filter 1406, an extension of conduit 1013C between connector 1011N of bag 1018 and that filter 1406, an extension of conduit 1013B between connector 1011M of bag 1018 and that filter 1406, and lastly an extension of conduit 1013J between connector 1011Q and that filter 1406.

Other conduits (not shown in FIG. 10) are added by the operator, and in particular the conduits leading to the source, buffer, cleaning liquid, rinsing liquid, collecting and waste containers respectively 1410, 1423, 1418, 1419, 1408, 1400 and 1412, and to filter 1401.

The installation is thus ready for the tangential filtration treatment described earlier.

In variants that are not illustrated:
the chromatography treatment installation further comprises a safety pressure sensor between the pump and the flow meter;
the chromatography treatment installation does not comprise any flow meter, and/or any bubble trap, and/or any filter;
the chromatography column is replaced by an ion exchange column or a membrane-based adsorbent;
the feed unit of the first installation is wheel-mounted;
the instrumentation platforms of the first installation are mounted perpendicularly to the press, and thus to the inclined chassis of the first cart, rather than being mounted parallel;
the tangential filter of the third cart of the second installation is of greater size or smaller size, depending on the volume of biological liquid to treat, and, the case arising, the tank has a suitable volume (in particular 50 liters, 100 liters, or 200 liters);
the tank of the third cart of the second installation has a double jacket, the outer one being of stainless steel, and the internal one of plastic, or vice-versa, or both are of stainless steel;
the tank of the third cart of the second installation is refrigerated and/or heated;
the tank comprises a door that is glazed at the location of the opening for the introduction of the bag;
the weight receiving members of the tank of the third cart of the second installation are controlled in centralized manner, via pneumatic, mechanical, hydraulic or electrical controlling and operating means;
the tank rests on more than three weight gauges, or fewer; and
the weight gauges are replaced by a radar probe for detecting the level of liquid in the tank to determine the volume therein;

In still another variant that is not illustrated, the tank is pivotally mounted on a U-shaped bracket situated in a plane parallel to the lateral faces of the third cart, the ends of which are fastened to the internal metal chassis. A handle fastened to the free end of the cylindrical lateral wall of the tank enables it to be easily pivoted about an axis perpendicular to the front face, between an operating position and an installation position. Pins disposed on each of the uprights of the bracket in the vicinity of axis, are adapted to cooperate with two discs fixed to the cylindrical lateral wall of the tank to lock it in the desired position, or, on the contrary, to free it to rotate. The locking is achieved by the insertion of a metal rod situated at the end of each pin into a bore of the corresponding disc. Conversely, to free the tank to rotate, it suffices to pull on each of the pins in order to make the rods come out of the discs. In its operating position, the tank is upright, such that its frustoconical bottom wall is turned towards the ground; the feed container being disposed within the tank, its apertures projecting from that bottom wall towards the ground. In its installation position, the tank lies down, the free end of its cylindrical lateral wall being arranged to face an opening of the lateral face of the third cart. This installation position facilitates for the operator the removal of a used feed container and the installation of a new one, which feed container is, the case arising, installed by the opening above the tank, contrary to tank 1083 which comprises an access door 1088. On putting the installation into operation and after the tank has been placed in its operating position, a pin is adapted to lock the tank in that position throughout the duration of the filtration process. Once the process is terminated, this pin is removed to unlock the tank so that it can pivot freely.

In still another variant not illustrated, the tank is pivotally mounted in the way described earlier, with or without assistance for the pivoting. The assistance for the pivoting of this tank is implemented by a rack-based system or by a gas spring.

In another variant that is not illustrated, the first and second carts and the biological liquid feed unit are adapted to equip an installation for treatment by dead-end filtration.

It should be noted more generally that the invention is not limited to the examples described and represented.

The invention claimed is:

1. An installation assembly comprising a pump cart for a biological liquid treatment installation for carrying out different types of treatment, which installation further comprises a conveying network cart, said conveying network cart comprising a network circuit portion between a plurality of connections and having a plurality of circuits;
wherein said pump cart has a first lateral face, a second lateral face by which it is configured to be juxtaposed against said conveying network cart and a front face meeting the two said lateral faces;
said pump cart further comprising:
at least one pump positioned to make liquid flow through said network circuit portion;
a pump support on which is mounted said at least one pump; and
a guide member to render said at least one pump movable in translation and on which said pump support is mounted;
said pump support being movable in translation in a direction going from the first lateral face towards the second lateral face of said pump cart;
whereby said at least one pump is disposed at a predetermined location among a plurality of locations on said pump cart depending on which one of said different types of treatment is carried out.

2. The installation assembly according to claim 1, wherein said guide member comprises two arms spaced apart by slide rods which are furthermore each fastened to each of the two said arms, and the movable pump support comprises a vertical block slidingly mounted on said rods.

3. The installation assembly according to claim 2, wherein said vertical block comprises a system for locking said vertical block against movement in translation on said rods.

4. The installation assembly according to claim 2, wherein said movable pump support comprises a receptacle mounted on a face of said vertical block and configured to receive said at least one pump.

5. The installation assembly according to claim 4, wherein said face of said vertical block is provided with means for hooking said receptacle, and said receptacle is provided with complementary hooking means for its mounting on said face of said block.

6. The installation assembly according to claim 5, wherein said face of said vertical block is equipped with several said hooking means provided at predetermined locations.

7. The installation assembly according to claim 4, wherein said receptacle has a front having a cut-out configured to receive a connecting head of said at least one pump.

8. The installation assembly according to claim 2, wherein said movable pump support and the two said arms are disposed on an upper face of said cart.

9. The installation assembly according to claim 1, further comprising a handle which is movable between a withdrawn position and an extended position in which said movable handle enables said cart to be moved.

10. The installation assembly according to claim 9, wherein said movable handle is removable.

11. The installation assembly according to claim 1, further comprising an internal space situated under an upper face and between the two said lateral faces, said space being configured to receive, at least partially, a biological liquid feed unit.

12. The installation assembly according to claim 11, further comprising a removable panel on said lateral first face which is configured to cover said internal space.

13. The installation assembly according to claim 1, further comprising at least one additional pump which is mounted in superposed configuration on said movable pump support relative to said at least one pump.

14. An installation for treating a biological liquid, comprising:
   a pump cart according to claim 1;
   a conveying network cart juxtaposed against said second lateral face of said pump cart, which conveying network cart comprises a portion of circuit having a plurality of connectors and a network for conveying liquid between said connectors, said conveying network being formed by a plurality of conduits, and a press comprising a first shell and a second shell mounted on said first shell, said first shell and second shell cooperating to form said conduits of said conveying network; and
   a biological liquid feed unit juxtaposed against said first lateral face of said pump cart, which feed unit is configured to feed said at least one pump with biological liquid;
   said at least one pump being located facing a connector of a said conduit and being configured to make said biological liquid flow in said conduit.

15. An installation according to claim 14, wherein at least one of said conveying network cart and said feed unit is configured to be nested at least partially within said pump cart.

16. An installation according to claim 14, wherein said feed unit comprises a tank configured to receive a feed container provided to contain said biological liquid, at least one measuring cell for measuring the weight of said tank, said tank resting on said at least one measuring cell when said feed unit is in a working configuration, and at least one weight receiving member for receiving the weight of said tank, said weight receiving member configured such that said tank no longer rests on said at least one measuring cell when said feed unit is in a resting configuration.

17. An installation according to claim 16, wherein said at least one measuring cell is interposed between two plates, one of which is fastened to said tank and the other to said feed unit, and said weight receiving member is formed by a cam interposed between the two said plates and by a crank configured to move said cam so as to move the two said plates apart.

18. An installation according to claim 16, wherein said feed unit comprises the same number of weight receiving members as there are measuring cells.

19. An installation according to claim 14, wherein said feed unit has a first lateral face provided with a plurality of valves and a second lateral face which is an opposite face to said first lateral face and which faces said pump cart.

20. An installation according to claim 14, wherein said conveying network cart comprises a base having a front face, a movable or removable door, said first shell being disposed on said front face of said base and said second shell being disposed in said door, said conveying network cart having a closed door position in which said conduits are formed, said second shell furthermore being of transparent material and said door being at least partly of transparent material.

21. An installation for treating a biological liquid, comprising:
   a pump cart according to claim 1;
   a conveying network cart juxtaposed against said second lateral face of said pump cart, which conveying network cart comprises a portion of circuit having a plurality of connectors and a network for conveying liquid between said connectors, said conveying network being formed by a plurality of conduits, and a press comprising a first shell and a second shell mounted on said first shell, said first shell and second shell cooperating to form said conduits of said conveying network; and
   a biological liquid feed unit mounted on said pump cart, which feed unit is configured to feed said at least one pump with biological liquid;
   said at least one pump being located facing a connector of a said conduit and being configured to make said biological liquid flow in said conduit.

* * * * *